(12) United States Patent
Li et al.

(10) Patent No.: US 8,767,209 B2
(45) Date of Patent: Jul. 1, 2014

(54) BROADBAND POLARIZATION SPECTROMETER WITH INCLINED INCIDENCE AND OPTICAL MEASUREMENT SYSTEM

(75) Inventors: Guoguang Li, Beijing (CN); Tao Liu, Beijing (CN); Edgar Genio, Beijing (CN); Tiezhong Ma, Beijing (CN); Yan Xiaolang, Beijing (CN)

(73) Assignee: Beioptics Technology Co., Ltd., Beijing (CN)

( * ) Notice: Subject to any disclaimer, the term of this patent is extended or adjusted under 35 U.S.C. 154(b) by 0 days.

(21) Appl. No.: 13/701,698

(22) PCT Filed: May 30, 2011

(86) PCT No.: PCT/CN2011/000916
§ 371 (c)(1),
(2), (4) Date: Dec. 3, 2012

(87) PCT Pub. No.: WO2011/150673
PCT Pub. Date: Dec. 8, 2011

(65) Prior Publication Data
US 2013/0070234 A1    Mar. 21, 2013

(30) Foreign Application Priority Data
Jun. 2, 2010    (CN) .......................... 2010 1 0199230

(51) Int. Cl.
*G01J 4/00* (2006.01)
*G01N 21/21* (2006.01)

(52) U.S. Cl.
CPC .............. *G01N 21/211* (2013.01); *G01N 21/21* (2013.01)
USPC ....................................................... 356/369

(58) Field of Classification Search
CPC ................................................... G01N 21/211
USPC ............................................... 356/364–369
See application file for complete search history.

(56) References Cited

U.S. PATENT DOCUMENTS 6,128,085 A    10/2000    Buermann
6,132,710 A    10/2000    Panigrahi et al.
(Continued)

FOREIGN PATENT DOCUMENTS

CN    1782695 A    6/2006
JP    1217240 A    8/1989
(Continued)

OTHER PUBLICATIONS

Sanders et al.; Invited Review: The Scientific Basis of *Lactobacillus acidophilus* NCFM Functionality as a Probiotic; Dairy and Food Culture Technologies, Department of Food Science, North Caroline State University.

(Continued)

*Primary Examiner* — Tarifur Chowdhury
*Assistant Examiner* — Md Rahman
(74) *Attorney, Agent, or Firm* — Fay Sharpe LLP

(57) ABSTRACT

An oblique incidence broadband spectroscopic polarimeter which is easy to adjust the focus, achromatic, maintains the polarization and has simple structure is provided. It comprise at least one polarizer (P, A), at least one curved reflector element (OAP1, OAP2, OAP3, OAP4) and at least two flat reflector elements (M1, M2). By utilizing the flat reflector element, the oblique incidence broadband spectroscopic polarimeter can change the propagate direction of beam, and compensate the polarization changes caused by the reflective focusing unit, make the polarization of beam passed the polarizer unchanged when obliquely incident and focus on the sample surface. The oblique incidence broadband spectroscopic polarimeter can accurately measure the optical constants of sample material, film thickness, and/or the critical dimension (CD) properties or three-dimensional profile for analyze the periodic structure of the sample. An optical measurement system including the oblique incidence broadband spectroscopic polarimeter is also provided.

28 Claims, 8 Drawing Sheets

(56) References Cited

U.S. PATENT DOCUMENTS

| | | | |
|---|---|---|---|
| 7,755,775 B1* | 7/2010 | Li | 356/625 |
| 2002/0006432 A1 | 1/2002 | Collins et al. | |
| 2002/0180991 A1 | 12/2002 | Takoudis | |
| 2006/0164642 A1* | 7/2006 | Amary et al. | 356/369 |
| 2007/0297034 A1* | 12/2007 | Zaghloul et al. | 359/108 |
| 2009/0073421 A1* | 3/2009 | Jung et al. | 356/73 |
| 2009/0109438 A1 | 4/2009 | Fukue | |
| 2009/0122317 A1* | 5/2009 | Ito et al. | 356/440 |
| 2011/0203357 A1* | 8/2011 | Prater et al. | 73/105 |

FOREIGN PATENT DOCUMENTS

| | | | |
|---|---|---|---|
| WO | 9917788 A1 | 4/1999 | |
| WO | 0197822 A1 | 12/2001 | |

OTHER PUBLICATIONS

Daniel et al.; Selecting Lactic Acid Bacteria for Their Safety and Functionality by Use of a Mouse Colitis Model, Applied and Environmental Microbiology, Sep. 2006, p. 5799-5805.

Tejada-Simon et al.; Ex Vivo Effects of Lactobacilli, Streptococci, and Bifidobacteria Ingesion on Cytokine and Nitric Oxide Production in a Murine Model, Journal of Food Protection, vol. 62, No. 2, 1999, pp. 162-169.

Matsumoto et al.; Preventive Effects of Bifidobacterium and *Lactobacillus* Fermented Milk on the Development of Inflammatory Bowel Disease in Senescence-Accelerated Mouse P1/Yit Stain Mice, Digension 2001; 64:92-99.

Perdigon et al.; Interaction of lactic acid bacteria with the gut immune system; European Journal of Clinical Nutrition (2002) 56, Suppl 4, 521-526.

Morita et al.; Cytokine Production by the Murine Macrophase Cell Line J774.1 after Exposure to *Lactobacilli*, Biosci. Biotechnol. Biochem. 66 (9), 1963-1966, 2002.

Rangavajhyala et al.; Nonlipopolysaccharide Components(s) of *Lactobacillus acidophilus* Stimulate(s) the production of Interleukin-la and Tumor Necrosis Factor-a by Murine Macrophages; Nutrition and Cancer, 2R(2) 130-134.

Zavaglia et al.; Isolation and Characterization of Bifidobacterium Strains for Probiotic Formulation; Journal of Food Protection, vol. 61, No. 7, 1998, pp. 865-873.

Schultz, Probiotics and Inflammatory bowel Disease, Am J Gastroenterol, 2000.

Lewis et al. Review article: the use of biotherapeutic agents in the prevention and treatment of gastrointestinal disease; Ailment Pharmacol Ther 1998: 12: 807-822.

Morata de Ambrosini et al.; Study of Adhesion of *Lactobacillus* casei CRL 431 to Ileal Intestinal Cells of Mice; Journal of Food Protection, vol. 62, No. 12, 1999, pp. 1430-1434.

* cited by examiner

BROADBAND POLARIZATION SPECTROMETER WITH INCLINED INCIDENCE AND OPTICAL MEASUREMENT SYSTEM

FIELD OF THE INVENTION

The present invention generally relates to an oblique incidence broadband spectroscopic polarimeter containing at least one polarizer, at least one curved reflector element and at least two flat reflector elements, more particularly, relates to an oblique incidence broadband spectroscopic polarimeter by using flat reflector element to change the propagation direction of the beam, achieving that the detecting beam can focus on the surface of the sample at oblique incidence. Further, the present invention also relates to an optical measurement system including such oblique incidence broadband spectroscopic polarimeter.

BACKGROUND OF THE INVENTION

Generally, a key step in optical measurement is to make the detecting beam focused onto the sample. Two methods are currently widely used. One method is to separate the last focusing lens from other components and only adjust the focusing lens to focus the detecting beam onto the sample. An example was illustrated in FIG. 1, the focusing is achieved by moving the last focusing lens up and down. Another method is to adjust the whole optical measurement system to focus the detecting beam on the sample. For example, as shown in FIG. 2, the focusing is achieved by moving the whole optical system up and down (for example, refer to the U.S. Pat. No. 5,747,813 and U.S. Pat. No. 5,486,701).

With the rapid development of semiconductor industry, it becomes very important to apply optical measure technology to accurately measure the critical dimension (CD), spatial profile and material properties of three-dimensional structures formed by the single or multiple layer on wafer. The wafer surface may not be flat due to various reasons such as film stress on the wafer. Therefore, auto-focusing for each measurement point across the whole wafer is a key technique to achieve high accuracy and high throughput in semiconductor production line. Also it is widely known that focusing the broadband detecting beam into a small spot size on the sample surface is highly desired. The small spot size allows to measure the micro patterned structures and broadband spectrum is helpful for better measurement accuracy. There are some issues in the first method: lens usually has chromatic aberration which results in different wavelengths of light focusing on different locations and thus worsen the accuracy. It is also hard to find the lens materials with good transmission in the whole broadband wavelength range. The second method inherits the same problem of lens aberration and has additional technical challenges. It is not a trivial job to adjust the entire optical system to focus and high accuracy measurement is therefore difficult to be achieved.

A new method was proposed as the above reasons, that is, focusing the broadband detecting beam on the sample surface by using the curved reflector mirrors (for example, refer to U.S. Pat. No. 5,608,526 and U.S. Pat. No. 7,505,133B1, U.S. Patent Application Publication No. 2007/0247624A1 and Chinese patent application Publication No. 101467306A). This method has advantages as below: the reflector mirror does not produce chromatic aberration in whole wavelength range, and has high reflectivity in wide wavelength range.

However, although the application of curved mirrors does not produce chromatic aberration and thus improve the focus and the measure accuracy, compared with lens, it is more difficult to align the optical path with curved mirrors. The adjustment of focal point and spatial orientation of curved mirrors was constrained by the incident light, often requiring the simultaneous adjustment of the entire optical system for better control of the output optical path and focusing point. For example, (1) elliptical mirror: While the spatial location of two focusing point is relatively fixed, the adjustable range of optical path and focusing position is very limited by adjusting the individual elliptical mirror after the incident light path was corrected. (2) toroidal mirror: Although the two corresponding focusing points can be achieved in a certain range of incident angles, the spatial relationship of the two focusing points changes with the relationship between toroidal mirror and incident light. The correlations between two focusing points are complex and it is very difficult to achieve focusing. Another drawback is that its adjustable range is small and is easy to create image aberrations. (3) Off-axis parabolic mirrors: The adjustable range was very limited because the aberrations were resulted as the angle of off-axis parabolic mirrors changes relative to the direction of incident light. While a wide range of the focusing position can be achieved by moving the off-axis parabolic mirror along with the direction of the collimated light beam, the relative position of focusing point to the off-axis parabolic mirror center cannot be changed. This also limits the adjustable range of the focusing points. In summary, the use of a single curved mirror itself does not produce chromatic aberration, but it is difficult to adjust and control the direction of the optical path and focusing positions. Furthermore, the polarization of beam will be changed after reflected by a single mirror. Take an aluminum reflector mirror as an example, the reflection coefficient $r_s$ and $r_p$ of S and P polarized light were changed with the incident angle, the amplitude and phase difference between the S and P polarized light vary with the angle and the wavelength of incident beam. In short, because the polarization states S and P with the polarization direction orthogonal to each other have different reflectivity and phase change, after being reflected by a mirror, the polarization states of broadband beam varies, resulting the control of the change of beam polarization difficult (for example, refer to U.S. Pat. No. 6,829,049B1 and U.S. Pat. No. 6,667,805).

In addition, the beam polarization control capability of the spectrometer determines the scope of its applications. Take Optical Critical Dimension (OCD) equipment as an example. Such equipment is widely used in integrated circuit manufacturing lines for process controls. The OCD tools can measure the critical dimension (CD), three-dimensional profile of periodic pattern on sample surface, thickness and optical constants of multilayer film materials by collecting reflectance spectra and phase characteristics of the polarized beam from the sample surface and fitting numerical simulation results. For this kind of applications, the focusing system of spectrometer must be able to control the beam polarization in the process of focusing and optical signal collection in order to measure the sample accurately.

Furthermore, when the spectrometer without polarizer was used to measure the sample with periodic structures, as mentioned in China patent application No. 201010270454.2, the incident beam must be natural light because the rotation angle of incident beam cannot be adjusted relative to the anisotropic angle of samples. In theory, the natural light emitted from light source is required to arrive on the sample surface either maintaining absolutely polarization or passing through none of polarization components. The anisotropic samples cannot be measured if polarization states were not maintained; under this circumstance, the measured values change as the anisotropic samples rotate. Therefore, the spectrometer capable of measuring the anisotropic samples while without polarization control components included demands the high quality of optical element and the sophisticated adjustment of the optical path. The light reflected by the sample is partially polarized; starting from the light source to the detector, in theory, the polarization of the incident beam either was maintained completely or no polarization-sensitive component was present in the path. For example, if a polarization sensitive component was encountered in the path, a depolarizer is required, thus it will reduce the signal to noise ratio. Moreover, the above problem cannot be corrected by numerical methods.

SUMMARY OF THE INVENTION

In view of the above issues, an oblique incidence broadband spectroscopic polarimeter has been brought forward by the inventor of the invention. It has the following advantages: 1) the focus is easily adjusted, 2) no chromatic aberration is achieved, 3) the polarization properties are maintained, and 4) configuration is simple. The oblique incidence broadband spectroscopic polarimeter comprises at least one polarizer, at least one curved reflector element and at least two flat reflector elements. Specifically, the oblique incidence spectroscopic polarimeter achieves the detecting beam focus on the sample surface at oblique incidence by using flat reflector element to change propagation direction of beam.

The present invention provides an oblique incidence spectroscopic polarimeter including a light source, a first focusing unit, a first polarizer, a first curved reflector element, a first flat reflector element, a second flat reflector element, a second focusing unit and detector unit, wherein the first focusing unit is used to focus a beam from the light source into a collimated beam; the first polarizer is used to change the collimated beam into a polarized beam; the first curved reflector element is used to focus the polarized beam and reflect the polarized beam to the first flat reflector element; the first flat reflector element is used to obliquely focus the polarized beam from the first curved reflector element on the sample; the second flat reflector element for reflect the beam from the sample to the second focusing unit; the second focusing unit for make the reflected beam from the second flat reflector element incidence on the detector unit, as well as focus on the sample; and the first flat reflector element and first curved reflector element meet the condition that incidence planes of the beams are perpendicular or parallel to each other.

In addition, the oblique incidence broadband spectroscopic polarimeter may also include a second curved reflector element and a second polarizer, the second curved reflector element set in the optical path between the second flat reflector element and the second polarizer, the second polarizer set in the optical path between the second curved reflector element and the second focusing unit, thereinto, the second curved reflector element for receive the reflected beam from the second flat reflector element and focusing the reflected beam into a collimated beam; the second polarizer is used to change the collimated beam from the second curved reflector element into polarized beam; the second focusing unit for making the polarized beam from the second polarizer focus and incidence on the detector unit; and the second flat reflector element and second curved reflector element meet the condition that incidence planes of the beams are perpendicular or parallel to each other.

In addition, the first flat reflector element and the first curved reflector element may have the same reflective materials and coating structures and meet the condition that incidence angles of the beams are same and the incident planes are perpendicular to each other, and the second flat reflector element and second curved reflector element may have the same reflective materials and coating structures and meet the condition that incident angles of beam are the same and the incident planes are perpendicular to each other.

In present invention, the first and second polarizer can be thin-film polarizer, Glan-Thompson prism polarizer, Rochon prism polarizer, Glan-Taylor prism polarizer, Glan laser polarizer. In particular, the first and second polarizers are Rochon prism polarizer and the material is preferred to $MgF_2$.

In present invention, the beam incident angles on the first flat reflector element and first curved reflector element, and on the second flat reflector element and second curved reflector element can be the same, and in the range of 10 degree to 45 degree. In addition, the incident angle of the beam on the sample surface can be in the range of 5 degree to 75 degree.

The present invention also provides an optical measurement system which includes the oblique incidence broadband spectroscopic polarimeter.

A further understanding of the nature and advantages of the inventions herein may be realized by reference to the preferred embodiment of remaining sections of the specifications and the attached drawings.

BRIEF DESCRIPTION OF THE DRAWINGS

In the attached drawings, all of views are not always on scale and the same reference signs in different drawings always represent basically the same elements. The same reference sign with different letter suffix represents the different instances of basically the same components.

DETAILED DESCRIPTION OF THE EMBODIMENTS

The terminologies in the specification are used only for the purposes of described, not for restrictive purposes. Unless otherwise stated, the terminologies used in this invention are consistent with their generic meanings.

(Principle of Focusing)

As mentioned above, in prior art, although the use of curved mirror itself does not produce chromatic aberration, it is difficult to align the light path direction and control the focus position by simple adjustment. In view of this reason, the inventors of the present invention propose the method of adjusting focus point and optical path by using two flat reflector mirrors on the condition that the detecting beam is oblique incident on the sample surface. Below with reference to FIGS. 3a to 3e, the method is described in detail.

Figure 1:
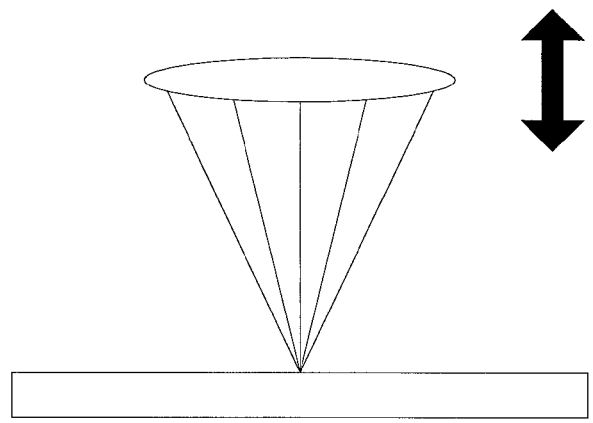
FIG. 1 is a schematic drawing to illustrate the realization of the focus by moving up and down the last focusing lens in prior art.
Figure 2:
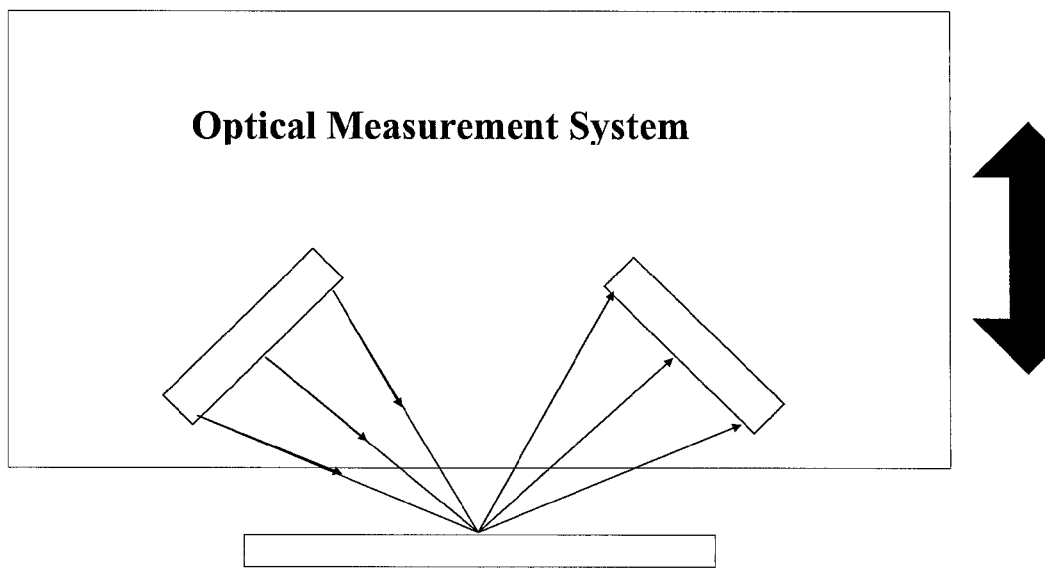
FIG. 2 is a schematic drawing to illustrate of the realization of the focus by moving the entire optical system in prior art.
Figure 3A:
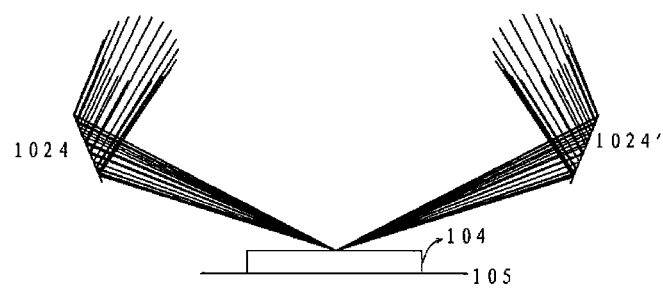
FIG. 3a to FIG. 3e are the schematic drawings to illustrate a method of adjusting focus by using two flat reflector mirrors.
Figure 3B:
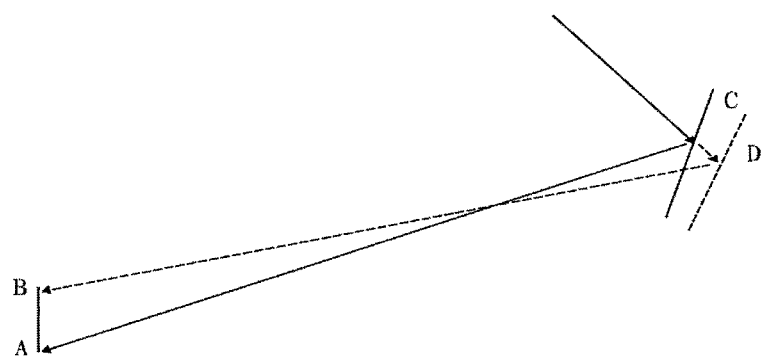

In FIG. 3a, assuming that the flat reflector mirror 1024 is the incident flat reflector mirror, the flat reflector mirror 1024' is the exit flat reflector mirror, and the incident planes of the flat reflector mirror 1024 and 1024' and the sample 104 are same. Incident flat reflector mirror 1024 can make the focusing detecting beam incident on the surface of sample 104 at arbitrarily angle (not limited to 90 degree). Then, the sample reflects the detecting beam to the exit flat reflector mirror 1024'. Then, the exit flat reflector mirror 1024' reflects the detecting beam to the other components (not shown in the figure). As shown in FIG. 3b, to move the focus position of the detecting beam vertically from A to B, it has CD+DB=CA and can be achieved by moving flat reflector mirror from C to D and adjusting the angle of inclination of the flat reflector mirror. The moving distance and angle of inclination of the flat reflector mirror can be calculated by computer program.

Figure 3C:
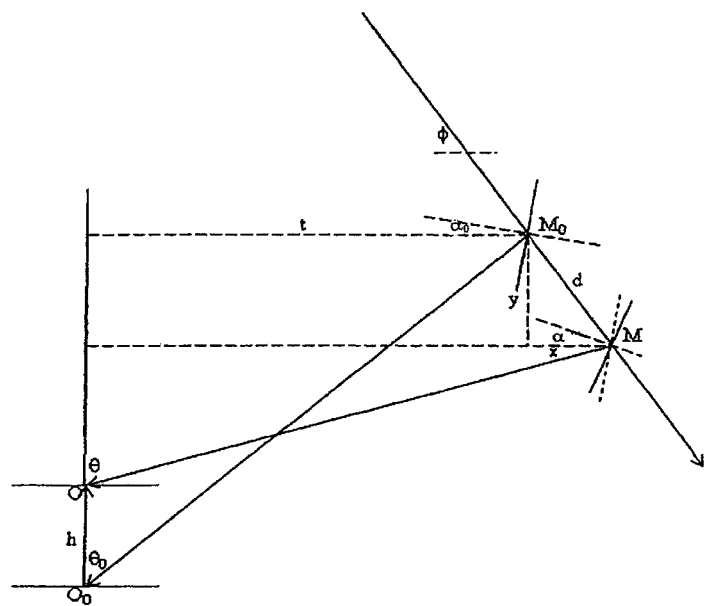

The specific method for calculation of the moving distance and tilt angle of flat reflector mirror as follows:

Shown in FIG. 3c, the angle between the chief ray of focusing incident detecting beam light and the horizontal plane is $\phi$, after reflected by the flat reflector mirror at the initial position $M_0$, the chief ray is incident on the sample at the incident angle $\theta_0$. When the flat reflector mirror move from the initial position $M_0$ to the position M (in the direction of the chief ray, the distance from the initial position $M_0$ to the position M is d) and tilt a angle of $(\alpha-\alpha_0)$ (here, $\alpha_0$ is the angle between normal line of flat reflector mirror in position $M_0$ and horizontal plane, $\alpha$ is the angle between normal line of flat reflector mirror in the position M and the horizontal plane), after reflected by the flat reflector mirror in the position of M, the chief ray of the incident detecting beam is incident on the sample at the incidence angle of $\theta$. Assuming the horizontal distance between center position of the flat reflector mirror in the initial position $M_0$ and the focus position $O_0$ (or O) is t, and the horizontal distance between center position of the flat reflector mirror in the position M and the focus position $O_0$ (or O) is t+x.

Based on geometrical optics structure in FIG. 3c, the following equations can be obtained:

$MO+d=M_0O_0$;

$MO = \dfrac{t+x}{\sin\theta}$;

$x=d\cos\phi$;

$MM_0=d$; and $M_0O_0 = \dfrac{t}{\sin\theta_0}$ d can be solved as:

$$d = \dfrac{t(\sin\theta - \sin\theta_0)}{\sin\theta_0(\sin\theta + \cos\phi)} \quad (1)$$

In addition, the angle $\alpha$ and $\alpha_0$, between the normal line of the surface of flat reflector mirror and the horizontal plane, satisfy the following relations:

$$\alpha_0 = \dfrac{(\phi + 90° - \theta_0)}{2} - (90° - \theta_0) \quad (2)$$

$$\alpha = \dfrac{(\phi + 90° - \theta)}{2} - (90° - \theta) \quad (3)$$

By the formula (2) and (3), can be obtained:

$$\alpha - \alpha_0 = \dfrac{\theta - \theta_0}{2} \quad (4)$$

Then, the vertical distance h between focus position $O_0$ and O is:

$h=tctg\theta_0-(t+x)ctg\theta-d\sin\phi=t(ctg\theta_0-ctg\theta)-d(\cos\phi ctg\theta+\sin\phi)$ Adjusting the focus height of the detecting beam must be accompanied with the variation of incident angle. Usually, the wafer surface and the sample stage can maintain relatively high flatness. If assume h changes 20 microns, t is 25 mm; $\theta_0=60°$ and $\phi=90°$, after adjust the focus, the angle of incidence changes about 0.01 degree. Such small rotation will still maintain polarization of arbitrary polarized beam without adjusting any other device. High precision rotation can be achieved through the piezoelectric-controlling rotary stage (for example: the U.S. Discovery Technology International, LLLP PRS-1 piezoelectric rotary stage), the precision can reach 0.0005 degree, resolution of up to 0.001 degree.

Figure 3D:
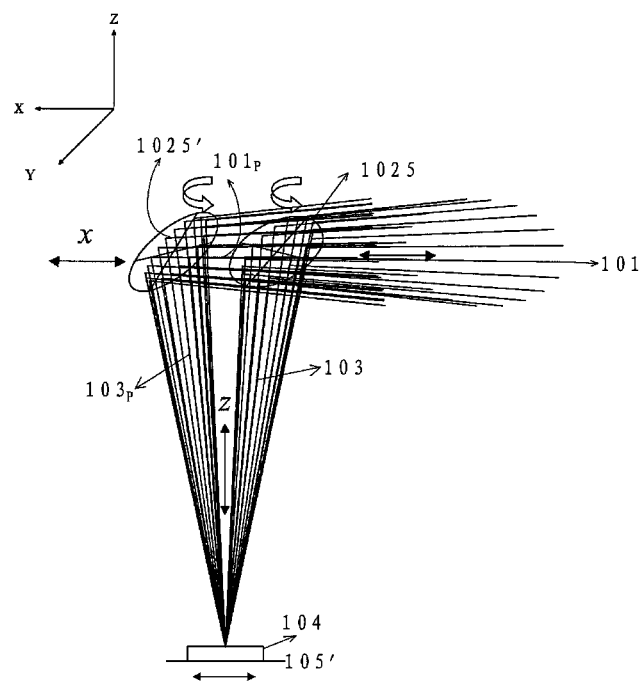

In FIG. 3d, assuming that the flat reflector mirror 1025 and 1025' are the incident and exit flat reflector mirror respectively. In the figure, the sample 104 is placed on an adjustable sample platform 105. Assuming that sample platform 105 in the horizontal plane (i.e., XY plane), the chief ray 101 of the focused beam is approximate parallel to the sample (semiconductor sample such as wafer) surface and propagate along the direction from right to left (i.e., X-direction). The focused beam is incident on the flat reflector mirror 1025, its chief ray 101 is incident on the flat reflector mirror 1025 at angle of 45 degree. In this case, according to the law of reflection, it shows that the chief ray 103, reflected by the flat reflector mirror 1025, deflects 90 degree relative to the incident chief ray 101. The angle between incident plane on flat reflector mirror 1025 and the sample surface can be any angle in 0-90 degree. In FIG. 3d, the reflected chief ray 103 is nearly normal incident on the sample 104. Therefore, the beam reflected by flat reflector mirror 1025 beam focused on the surface of the sample 104. After reflected by the surface of sample 104, the beam is incident on the flat reflector mirror 1025', the reflected chief ray 103$_p$ is reflected by sample surface and is incident on the flat reflector mirror 1025' at angle of incidence 45 degree. In this case, according to the law of reflection, chief ray 101$_p$, reflected by flat reflector mirror 1025', deflects 90 degree relative to the reflected chief ray 103$_p$, in other words, the chief ray 103 approximately propagates along the negative X direction away from flat reflector mirror 1025'. When adjusting the focus position in the vertical direction (that is, Z direction), in order to keep the focus position in the Y direction, the two flat reflector mirrors should move horizontally along the X direction and tilt with mirror symmetry or mirror antisymmetry. At the same time, sample has to move along the X direction with the focus position. Computer program can be used to adjust the amount of movement and angle of inclination of the flat reflector mirror, as well as the amount of movement of the sample.

Figure 3E:
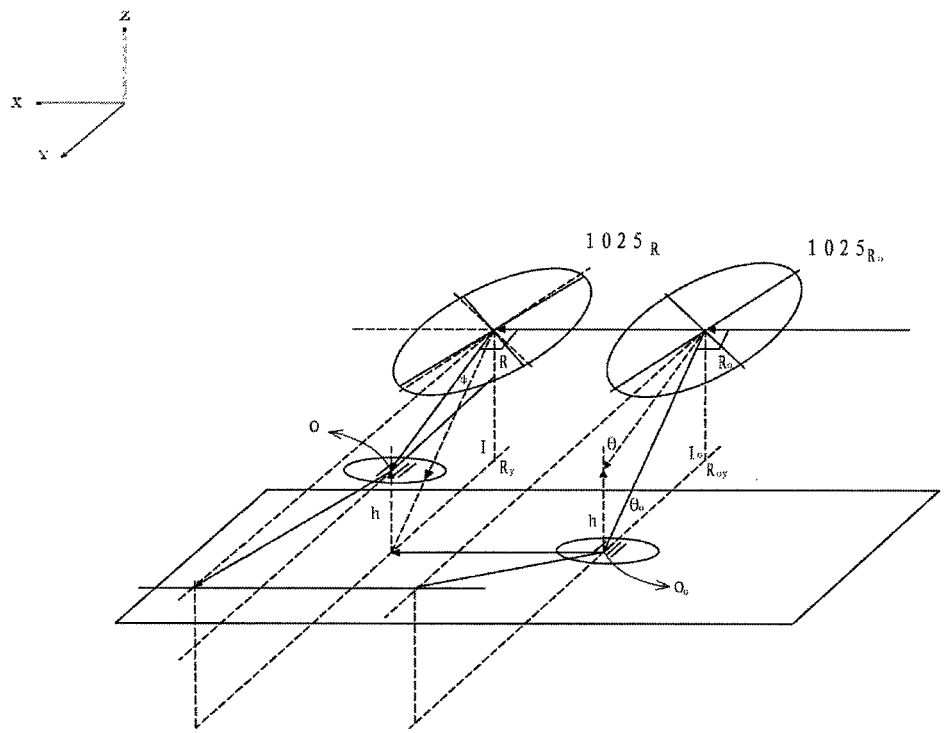

With reference to FIG. 3e, the amount of the movement and inclination angle of the flat reflector mirror and the movement amount of the sample can be explained as below. The focused beam propagates along the X direction; To be noticed, in FIG. 3, it only shows the propagation direction of the chief ray of the focused beam. After reflected by the flat reflector mirror (for example flat reflector mirror 1025 at position $R_0$), the beam focused on the position of sample center $O_0$. After reflected by the flat reflector mirror 1025$_{R0}$, the chief ray is 90 degree to the direction X, the chief ray is incident on the sample and the chief ray of reflected beam by the sample are in the plane $I_0$, and this plane $I_0$ is perpendicular to the plane of sample. The reflected beam by sample is incident on the flat reflector mirror (not shown in FIG. 3e) which is mirror symmetric or mirror antisymmetric to the flat reflector mirror at position $R_0$ (i.e., the flat reflector mirror 1025') and reflects reflected beam to the negative X direction. Assuming that the chief ray of the beam from flat reflector mirror 1025$_{R0}$ is incident on the sample center $O_0$ at incidence angle of $\theta_0$. Adjusted target angle of incidence is $\theta$ ($\theta > \theta_0$) (the flat reflector mirror 1025$_R$ in the target location R), the adjustment keeps the focus position unchanged in the Y direction, which simplifies the requirements to the sample platform. Assuming that the distance between the center of the flat reflector mirror 1025$_{R0}$ and sample center in the Y direction is $R_0$,$O_0$=S. Under this assumption, when the incidence angle was adjusted from $\theta_0$ to $\theta$, the changes of focusing position in the X direction is h=(ctg $\theta_0$–ctg $\theta$)*S, i.e., the optical path shortened S/sin $\theta_0$–S/sin $\theta$. Since the focal length of incident focused beam is unchanged, and optical path of the beam after passing through flat reflector mirror is shortened, the optical path before flat reflector mirror is required to be increased. With geometrical relation of $R_0O_0$=RO+RR$_0$, the optical path is reduced by RR$_0$=S/sin $\theta_0$–S/sin $\theta$. In the adjustment of flat reflector mirror, the first step is to move the flat reflector mirror for a distance of S/sin $\theta_0$–S/sin $\theta$ along propagation direction of the chief ray of the incident beam. After the above adjustment, the focus position is on the path of the original chief ray. The second step is to rotate the flat reflector mirror 1025 with the angle of $\phi$ ($\phi=\theta-\theta_0$), along the axis, which is the chief ray of incident beam to the mirror reflector 1025, the focused beam spot keeps in the incident plane to the sample. If, meanwhile, the flat mirror reflector that to collect light reflected by the sample has the adjustment mirror symmetric or antisymmetric to the flat mirror reflector 1025, and the sample platform should move the same distance S/sin $\theta_0$–S/sin $\theta$ along the X direction. finally, the focus position vertically moves up h=(ctg $\theta_0$–ctg $\theta$)*S. the original focus position of $O_0$ is moved to the new focus position O with change of incident angle.

In this case, adjusting the focus height of the detecting beam must be accompanied with the variation of incident angle. Usually the wafer surface and the sample stage can maintain high flatness, on the condition that h changes 20 microns, S is 25 mm, □ and $\theta_0$=30° (i.e., the incidence angle is) 60°, when adjust the focus, the angle of incidence changes less than 0.01 degree. High precision rotating can be achieve through the piezoelectric-controlling turntable (for example: the U.S. Discovery Technology International, LLLP PRS-1 piezoelectric turntable), the precision can reach 0.0005 degree, resolution of up to 0.001 degree.

Since the flat reflector mirror does not affect the focus condition of incident light and produce chromatic aberration, the use of reflecting mirror can maintain the beam quality while changing the beam propagation direction. In addition, on one hand, flat reflector mirrors are often used in folding optical path to make the whole optical system more compact. On the other hand, flat reflector mirrors can realize high reflectivity in broadband spectral range and have little influence on the light intensity; and with the aid of the focus judgment method, flat reflector mirror can realize the accurate manual or automatic focusing. Therefore, in present invention, the focus was realized by adjusting the flat reflector mirror.

(The Principle of Maintaining the Polarization Properties of Arbitrarily Polarized Light)

Figure 4A:
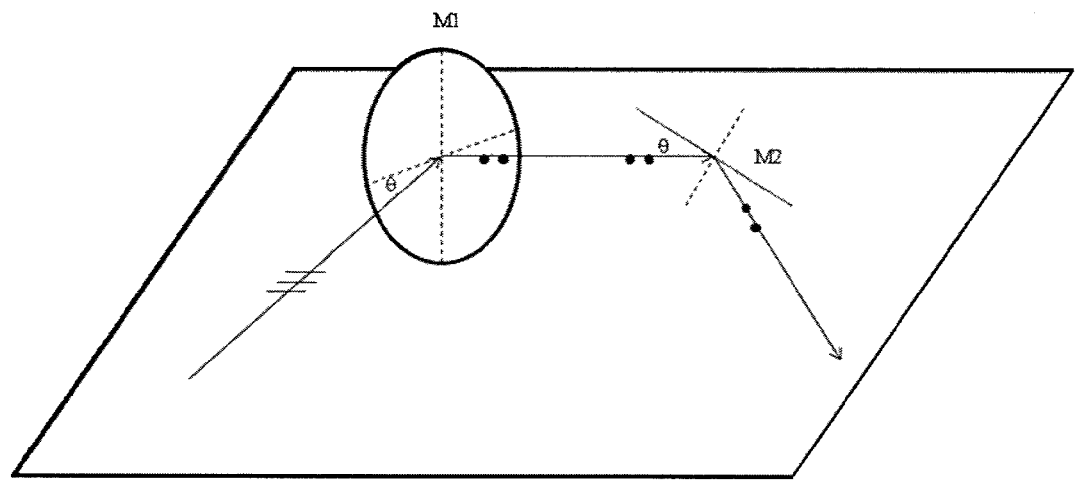
FIG. 4a to FIG. 4c are the schematic drawings to maintain polarization state of an optical beam.
Figure 4B:
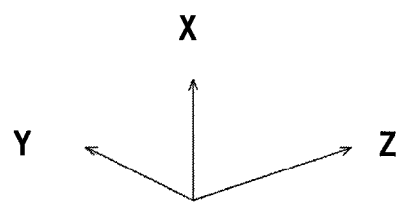
Figure 4B:
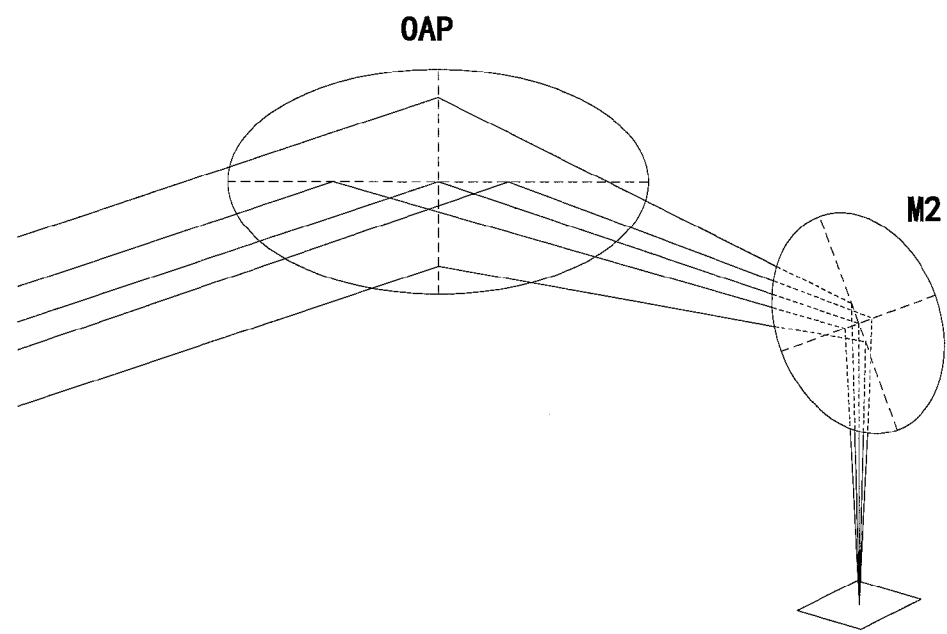

With reference to FIGS. 4a and 4b, the basic principles of maintaining polarization properties of polarized light through two flat reflector mirrors or a flat reflector mirror and an off-axis parabolic mirror can be explained as below.

As shown in FIG. 4a, assuming that the S (or P) polarized beam with the incident plane of the first flat reflector mirror M1 as reference enters M1 with the incident angle of (90-$\theta$) and is reflected to the second flat reflector mirror M2 by the first flat reflector mirror M1. If the incident plane on the first flat reflector mirror M1 is perpendicular to the incident plane on the second flat reflector mirror M2, and M2 is tilted to position that beam reflected by M1 is incident on M2 with the incident angle of (90-$\theta$), the S (or P) polarized light in the incident plane of M1 as reference will changes into P (or S) polarized light within the incident plane on M2 as reference after being reflected by M1.

Now analyze the changes of the propagation direction and the polarization state of the beam with the right-hand reference system established by taking the beam propagation direction as +Z direction. The above process can be expressed into a mathematical formula below:

$$\begin{cases} E_x = E_{1s} \\ E_y = E_{1p} \end{cases} \quad (a)$$

The polarization components $E_{1s}$, $E_{1p}$ with the incident plane on M1 as the reference are defined as +X and +Y direction component in the right-handed reference system respectively. After being reflected by M1, $$\begin{cases} E'_{1s} = r_{1s} E_{1s} \\ E'_{1p} = r_{1p} E_{1p} \end{cases} \quad (b)$$

$E_1'$, $E_{1p}'$ represent the polarization components of reflected light with the incident plane on M1 as reference; $r_{1s}$ and $r_{1p}$ represent the reflectance of S- and P-polarization on the first flat reflector mirror respectively, with incident plane on M1 as reference and incident on M1 with angle of (90-$\theta$). And, $$\begin{cases} E_{2s} = E'_{1p} \\ E_{2p} = -E'_{1s} \end{cases} \quad (c)$$

After reflected by M1, the $E_{1s}$ and $E_{1p}$ become the incident lights of M2 with the polarization components –$E_{2p}$ and $E_{2s}$ respectively, with the incident plane of M2 as reference. After reflected by M2, $$\begin{cases} E'_{2s} = r_{2s}E_{2s} \\ E'_{2p} = r_{2p}E_{2p} \end{cases} \quad (d)$$

$E_{2s}'$, $E_{2p}'$ represent the polarization components of reflected light with incident plane of M1 as reference, $r_{2s}$ and $r_{2p}$ represent the reflectivity on the second mirror M2 of the S-polarization and P-polarization respectively, which enter M2 with angle of (90−θ) and take incident plane of M2 as reference.

Due to the right-hand rule, the polarization direction of S-polarized light which takes incident plane of M1 as reference is the negative direction of the P-polarized light which takes incident plane of M2 as reference. Set the polarization direction of S-polarized beam which takes incident plane of M1 as reference is always along the positive direction of X-axis in the right-hand reference system which is established by taking the beam propagation direction as +Z direction. After the beam is reflected by M2, the polarization direction of P-polarized beam, with incident plane of M2 as reference, is in the positive direction of X-axis; so, the polarization direction of S-polarized beam, with incident plane of M2 as reference, is in the negative direction of Y-axis. Thus:

$$\begin{cases} E'_{2p} = E'_x \\ E'_{2s} = -E'_y \end{cases} \quad (e)$$

$E_x'$ and $E_y'$ represent the polarization components of reflected beam. In the case of M1 and M2 have the same reflective materials and coating structure:

$$\begin{cases} r_{1s} = r_{2s} \\ r_{1p} = r_{2p} \end{cases} \quad (f)$$

Based on the above formulae, there is:

$$\begin{cases} \dfrac{E_x}{E_y} = \dfrac{E'_x}{E'_y} \end{cases} \quad (g)$$

In the above formulae (a)-(g), all the variables are complex. The formula (g) shows that the ratio of the two polarization components of reflected light equals to that of the incident light. Therefore, with the above two flat reflector mirrors, the polarization properties of the incident light can be maintained.

According to the above formulae (a)-(e), as long as the first flat reflector mirror M1 and the second flat reflector mirror M2 satisfy the relation of $r_{2s}r_{1p}=r_{2p}r_{1s}$, the relationship in formula (g) can be maintained. That is, if two mirrors satisfy the relation $r_{2s}r_{1p}=r_{2p}r_{1s}$, then when passes through the two mirrors, polarization properties of the incident light can be maintained.

Therefore, in the system consisting of two flat reflector mirrors with the incident plane perpendicular to each other and with the same incident angle, the polarization properties of the incident light can be perfectly maintained. Additionally, in the case that one of the above two flat reflector mirrors was replaced with an off-axis parabolic mirror which has the same reflective material and coating structure as the other flat reflector mirror, the polarization properties of such a system was simulated under small numerical aperture (NA). Although the polarization properties of the beam will have deviations after passing the system constituted by the off-axis parabolic mirror and flat reflector mirror, when the collimated beam is focused with a small NA, the deviations of the polarization are not sufficient to affect the accuracy of measurement. For the strict polarization requirement, the measurement results can be further calibrated using numerical calculation.

Figure 4C:
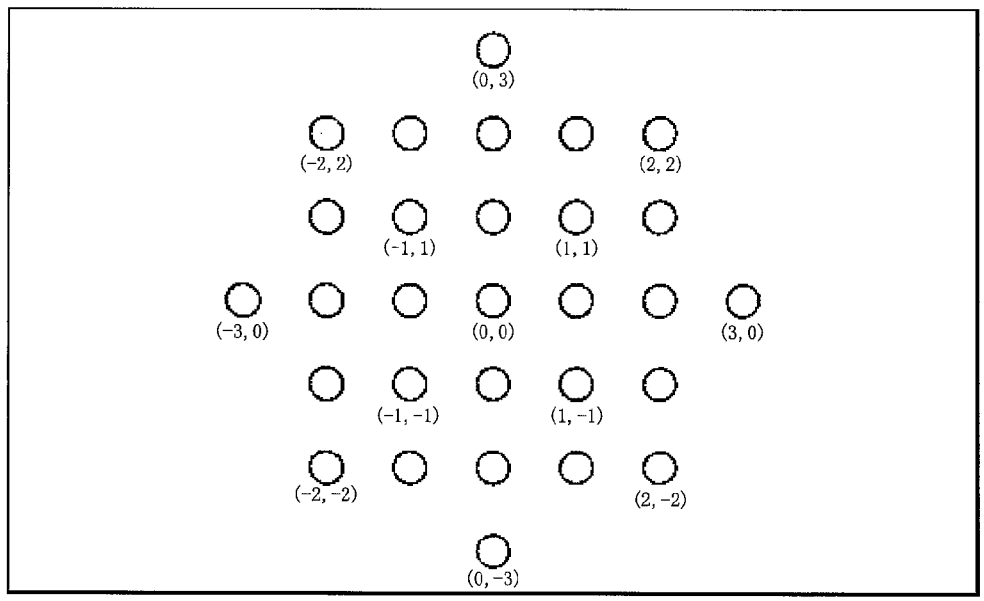

For example, as shown in FIG. 4b, a collimated beam is circularly polarized light before being incident on the off-axis parabolic mirror OAP, i.e., Ex=Ey, and Phase (Ex)−Phase (Ey)=90 degree, wherein, Ex and Ey are the amplitude of the electric vector of the beam in the x and y directions respectively, and Phase (Ex) and Phase (Ey) are the phase of the electric vector of the beam in the x and y directions respectively. After reflected by off-axis parabolic mirrors, the half-cone angle of focused beam is 4.2 degree (NA=0.073). Assuming the wavelength of incident light is 210 nm, the calculated spatial distribution within the cross-sectional of incident beam is shown in FIG. 4c(29 points in total, and already partially marked, for example, (0,3) to (0,0)). After numerical calculation, the intensities and phase changes of polarization in the focus point are listed in Table 1. Polarization intensity variation is defined as |Ex/Ey|−1, and the polarization phase variation is defined as Phase (Ex)−Phase (Ey)− 90. Because the intensity and phase variation of the polarized beam with a central symmetry of (0,0) are quite closely complementary, the above variations as a whole can be further alleviated.

TABLE 1

| cross-section distribution of calculated points | Polarization intensity variation | polarization phase variation (degree) | cross-section distribution of calculated points | Polarization intensity variation | polarization phase variation (degree) |
| --- | --- | --- | --- | --- | --- |
| (−3, 0) | 0.0011 | 2.1107 | (3, 0) | −0.0069 | −2.6477 |
| (−2, −2) | 0.0205 | 2.3577 | (2, 2) | −0.0244 | −2.1827 |
| (−2, −1) | 0.0106 | 1.8931 | (2, 1) | −0.0145 | −1.9597 |
| (−2, 0) | 0.0014 | 1.4637 | (2, 0) | −0.0039 | −1.7022 |
| (−2, 1) | −0.0071 | 1.0695 | (2, −1) | 0.0073 | −1.4099 |
| (−2, 2) | −0.0150 | 0.7107 | (2, −2) | 0.0193 | −1.0827 |
| (−1, −2) | 0.0212 | 1.5870 | (1, 2) | −0.0211 | −1.3694 |
| (−1, −1) | 0.0107 | 1.1563 | (1, 1) | −0.0117 | −1.1123 |
| (−1, 0) | 0.0010 | 0.7607 | (1, 0) | −0.0017 | −0.8203 |

TABLE 1-continued

| cross-section distribution of calculated points | Polarization intensity variation | polarization phase variation (degree) | cross-section distribution of calculated points | Polarization intensity variation | polarization phase variation (degree) |
|---|---|---|---|---|---|
| (−1, 1) | −0.0080 | 0.4004 | (1, −1) | 0.0091 | −0.4934 |
| (−1, 2) | −0.0164 | 0.0752 | (1, −2) | 0.0206 | −0.1315 |
| (0, −3) | 0.0329 | 1.1893 | (0, 3) | −0.0266 | −0.8739 |
| (0, −2) | 0.0212 | 0.7579 | (0, 2) | −0.0184 | −0.6175 |
| (0, −1) | 0.0102 | 0.3614 | (0, 1) | −0.0095 | −0.3263 |
| (0, 0) | 0.0000 | 0.0000 | | | |

Therefore, the system with the off-axis parabolic mirror and flat reflector mirror can also maintain the polarization properties of the incident light.

The above example only simulated the condition of replacing one of the two flat mirror flat reflector mirrors with an off-axis parabolic mirror with the same reflective material and coating structure. Not only flat mirror flat reflector mirror with off-axis parabolic mirror, but also other curve mirror, such as toroidal mirror, ellipsoidal mirror or non-quadric surface mirror, can the polarization properties of polarized light be essentially maintained as long as any two kinds of mirrors meet the above relations.

The Fresnel's law shows that, when reflected on the interface of two media, the reflection coefficient $r_p$, $r_s$ is, incidence, $r^p/r^s=-1$; the smaller angle of incidence, the smaller the impact caused by material properties. Therefore, when the two mirrors approximately have the same reflective material and coating structure and meet conditions that the incident angles of the chief ray are identical and the incident planes are perpendicular to each other, the small incident angle, theoretically is superior to the big incident angle, and is more conducive to reduce the deviation from the ideal situation. For example, with 15 degree of incident angle, under the same conditions as described in Table 1, the half-aperture angle of focused beam is 4.2 degree (NA=0.073). As seen from Table 2, when the incident angle is 15 degree, the intensity and phase variations of polarization are much less than the incident angle with 45 degree.

TABLE 2

| cross-section distribution of calculated points | Polarization intensity variation | polarization phase variation (degree) | cross-section distribution of calculated points | Polarization intensity variation | polarization phase variation (degree) |
|---|---|---|---|---|---|
| (−3, 0) | 0.003219 | 0.499604 | (3, 0) | −0.00893 | −0.71834 |
| (−2, −2) | 0.009241 | 0.296834 | (2, 2) | −0.01243 | −0.0084 |
| (−2, −1) | 0.005685 | 0.315199 | (2, 1) | −0.00919 | −0.24283 |
| (−2, 0) | 0.002784 | 0.356946 | (2, 0) | −0.00532 | −0.45411 |
| (−2, 1) | 0.000529 | 0.422081 | (2, −1) | −0.0008 | −0.64235 |
| (−2, 2) | −0.00109 | 0.510629 | (2, −2) | 0.00439 | −0.80766 |
| (−1, −2) | 0.008989 | 0.057144 | (1, 2) | −0.00865 | 0.157759 |
| (−1, −1) | 0.005021 | 0.112179 | (1, 1) | −0.00582 | −0.04011 |
| (−1, 0) | 0.001711 | 0.190486 | (1, 0) | −0.00235 | −0.21477 |
| (−1, 1) | −0.00095 | 0.292091 | (1, −1) | 0.001776 | −0.3663 |
| (−1, 2) | −0.00297 | 0.417043 | (1, −2) | 0.006562 | −0.49479 |
| (0, −3) | 0.013148 | −0.27524 | (0, 3) | −0.00729 | 0.484252 |
| (0, −2) | 0.008095 | −0.20663 | (0, 2) | −0.0055 | 0.299491 |
| (0, −1) | 0.003717 | −0.1149 | (0, 1) | −0.00307 | 0.138105 |
| (0, 0) | 0.000000 | 0.000000 | | | |

$$r_{12,p} = \frac{N_2\cos\theta_1 - N_1\cos\theta_2}{N_2\cos\theta_1 + N_1\cos\theta_2}; r_{12,s} = \frac{N_1\cos\theta_1 - N_2\cos\theta_2}{N_1\cos\theta_1 + N_2\cos\theta_2};$$

In the medium, when the light is reflected in the surface of the monolayer film, the reflection coefficient $r_p$, $r_s$ is, $$r^p = \frac{r_{12,p} + r_{23,p}\exp(-j2\beta)}{1 + r_{12,p}r_{23,p}\exp(-j2\beta)}; r^s = \frac{r_{12,s} + r_{23,s}\exp(-j2\beta)}{1 + r_{12,s}r_{23,s}\exp(-j2\beta)};$$

$$\beta = 2\pi\left(\frac{d}{\lambda}\right)N_2\cos\theta_2;$$

The above formula shows that, when incidence at a small angle, the sensitivity of $r^p$ and $r^s$ with the angle are low, that is, the sensitivity of polarization change is low; When at normal In prior art, there is the case of adopting a small incident angle to reduce the polarization change, such as U.S. Pat. No. 5,608,526, in which the embodiment contains only a single mirror. When adopting the embodiment described above that contains two mirrors have approximately the same reflective material and coating structure and meet the condition that the incident angles of the chief ray are the same and the incident planes are perpendicular to each other, its polarization maintaining is superior to that of a single mirror. Table 3 shows the condition that only has single mirror with 15 degree incident angle and without second flat reflector mirror. As shown in Table 3, the average changes in the polarization phase and polarization intensity are obviously inferior to the condition described in Table 2. Therefore, the technical solutions proposed in the present invention are superior to the existing technologies.

TABLE 3

| cross-section distribution of calculated points | Polarization intensity variation | polarization phase variation (degree) | cross-section distribution of calculated points | Polarization intensity variation | polarization phase variation (degree) |
|---|---|---|---|---|---|
| (−3, 0) | 0.004232 | 1.07876 | (3, 0) | −0.00573 | 1.13577 |
| (−2, −2) | 0.004625 | 1.033869 | (2, 2) | −0.00128 | 1.496409 |
| (−2, −1) | 0.004048 | 1.062921 | (2, 1) | −0.00223 | 1.313157 |
| (−2, 0) | 0.004079 | 1.097166 | (2, 0) | −0.00257 | 1.135153 |
| (−2, 1) | 0.004719 | 1.136599 | (2, −1) | −0.0023 | 0.96232 |
| (−2, 2) | 0.005969 | 1.181215 | (2, −2) | −0.00143 | 0.794585 |
| (−1, −2) | 0.004017 | 0.979498 | (1, 2) | 0.00143 | 1.422795 |
| (−1, −1) | 0.003365 | 1.043165 | (1, 1) | 0.00041 | 1.274277 |
| (−1, 0) | 0.003321 | 1.112003 | (1, 0) | −3.5E−06 | 1.13099 |
| (−1, 1) | 0.003885 | 1.186025 | (1, −1) | 0.00019 | 0.992879 |
| (−1, 2) | 0.005059 | 1.265246 | (1, −2) | 0.00099 | 0.859891 |
| (0, −3) | 0.004142 | 0.828326 | (0, 3) | 0.005255 | 1.46486 |
| (0, −2) | 0.002805 | 0.921517 | (0, 2) | 0.003546 | 1.345757 |
| (0, −1) | 0.002078 | 1.019823 | (0, 1) | 0.002448 | 1.231908 |
| (0, 0) | 0.00196 | 1.123276 | | | |

In summary, if the two mirrors have approximately same reflective material and coating structure and meet the condition that incident angles of the chief ray are the same and the incident planes of the chief ray are perpendicular to each other (within the allowed error range, that is, including the situation that incident angles are approximately the same and incident plane are nearly perpendicular to each other), the polarization properties of arbitrary incident light will remain unchanged after reflected by the two mirrors. The example of mirrors with the same reflective material and coating structure are the mirrors simultaneously coated in the same vacuum chamber.

In addition, in the case that the two mirrors do not have the same reflective material and coating structure and only meet the conditions of the beam incident planes perpendicular or parallel to each other, only when the detecting beam is linearly polarized and the polarization direction is perpendicular or parallel to the incident plane, the polarization properties can be remained unchanged.

In the case of described above, the incident angle changes less than 0.01 degree when adjust focus. Such a small change can remain polarization properties of arbitrary incident beam without adjusting any other device.

(Measuring Principle)

The reflectance of the sample can be expressed through Jones matrix as follows:

$$J_s = \begin{pmatrix} r_{pp} & r_{ps} \\ r_{sp} & r_{ss} \end{pmatrix} = r_{ss}\begin{pmatrix} \rho_{pp} & \rho_{ps} \\ \rho_{sp} & 1 \end{pmatrix}.$$

Jones matrix elements vary with the change of azimuth angle of incident plane and incident angle of detecting beam on sample surface. Normally, the uniform thin film is non-birefringent material, in the case of any azimuth and incident angle, $r_{ps}=r_{sp}=0$. For the thin film includes birefringent material, or the thin film composed by non-birefringent material and has surface periodic structure, such as the periodic shallow trench structure of silicon shown in FIG. 5, usually $r_{ps}$ and $r_{sp}$ are not equal to zero. But when any two of optical axis or structural axis are in the incident plane, $r_{ps}=r_{sp}=0$, the detailed instructions can be referred to the Spectroscopic Ellipsometry Principles and Applications, Hiroyuki and Fujiwara, 2007; in FIG. 5, when the azimuth angle φ=0 or 90 degrees, $r_{ps}=r_{sp}=0$.

(1) Absolute reflectivity measurement method. Oblique incidence broadband spectroscopic polarimeter can measure the sample Jones matrix element $r_{pp}$, $r_{ps}$, $r_{sp}$ and $r_{ss}$. Measuring the reflectivity of a sample can be done as follows:

a. Measure dark value $I_d$ of a spectrometer;
b. Measure the spectra of a reference sample, for example, the bare silicon wafer, and obtain the spectrum value $I_r$;
c. Measure the spectra of sample, and obtain the value I;
In this way, the reflectivity of the sample:

$$R=(I-I_d)/(I_r-I_d)\times R(\text{ref}).$$

Wherein, R(ref) is the absolute reflectivity of the reference sample. R(ref) can be obtained from other measurements, or through calculating the properties of the reference sample, R(ref) is usually from the reflectivity of bare silicon.

In the process of actual measurement, by adjusting the polarizer P and analyzer A, the absolute reflectivity can be measured when the polarization of P and A is set at combinations of directions corresponding to the sample's p&p, p&s, s&p, and s&s in incident plane respectively, then $\rho_{pp}$, $\rho_{ps}$, $\rho_{sp}$ and $\rho_{ss}$, can be obtained. If $r_{ps}=r_{sp}=0$, all that is needed are to adjust the polarizer P or analyzer A, then $r_{pp}$ and $r_{ss}$ can be measured.

Figure 5:
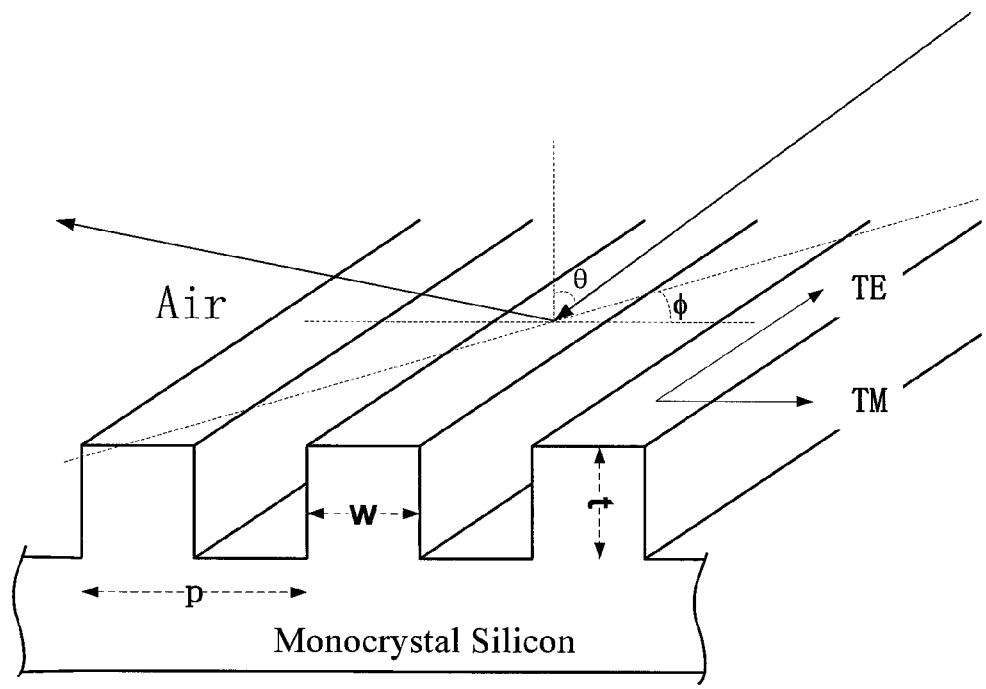
FIG. 5 is a block diagram of periodic shallow trench structure on monocrystal silicon.
Figure 6:
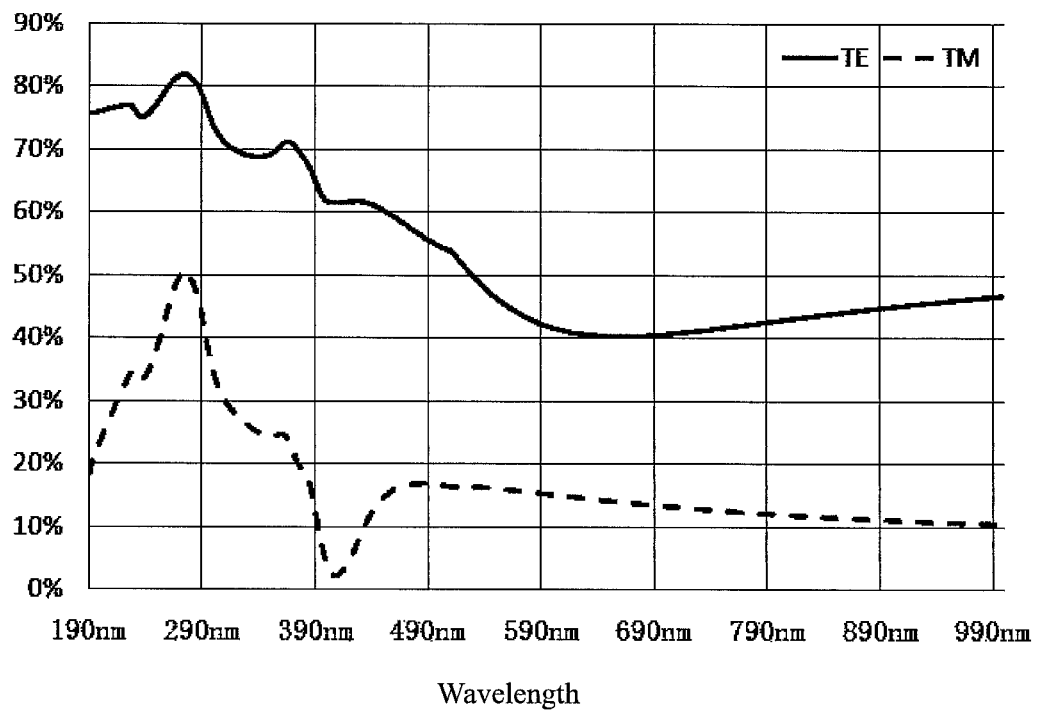
FIG. 6 is a schematic drawing to show the absolute reflectance spectra of TE and TM modes from monocrystal silicon periodic shallow trench in absolute reflectance measurements.

For example, in the one-dimensional grating structure, as shown in FIG. 5, the two orthogonal polarized directions are defined respectively as that the TM is the direction perpendicular to the lines and TE is the direction parallel to the lines. FIG. 6 shows, when the pitch p of 100 nm, line width w of 50 nm, groove depth t of 50 nm, □φ=0, θ=60°, □ the reflectivity of TE polarization (the dotted line) and the reflectivity of TM polarization (the solid line).

(2) Ellipsometry measurement method: the oblique incidence broadband spectroscopic polarimeter in present invention is equivalent to an ellipsometer of polarizer-sample-analyzer (PSA). Through measurement with rotating polarizer P and fixed analyzer A, or fixed analyzer A and rotating polarizer P, or rotating polarizer P and analyzer A at a certain frequency ratio, the Fourier coefficients can be calculated, and then the physical properties of the sample can be derived by comparing the measurements with the numerical simulation results through numerical regression. The detailed measurement principles can be referred to the principle formula in HANDBOOK OF ELLIPSOMETRY, Harland G. Tompkins, 2005; Spectroscopic Ellipsometry Principles and Applications, Hiroyuki and Fujiwara, 2007 and Liang-Yao Chen, Xing-Wei Feng, Yi Su, Hong-Zhou Ma, and You-Hua Qian, "Design of a scanning ellipsometer by synchronous rotation of the polarizer and analyzer," Appl. Opt. 33, 1299-

1305 (1994). The following is a brief description for the condition of rotating analyzer ellipsometer (RAE).

$$L_{out}=AR(A)J_sR(-P)PL_{in},$$

so, $$\begin{bmatrix} E_A \\ 0 \end{bmatrix} = E_{in} \begin{bmatrix} 1 & 0 \\ 0 & 0 \end{bmatrix} \begin{bmatrix} \cos A & \sin A \\ -\sin A & \cos A \end{bmatrix} \begin{bmatrix} r_{pp} & r_{ps} \\ r_{sp} & r_{ss} \end{bmatrix} \begin{bmatrix} \cos P & -\sin P \\ \sin P & \cos P \end{bmatrix} \begin{bmatrix} 1 & 0 \\ 0 & 0 \end{bmatrix} \begin{bmatrix} 1 \\ 0 \end{bmatrix}.$$

then, $$E_A = (\rho_{pp} + \rho_{ps} \tan P)\cos(A) + (\rho_{sp} + \tan P)\sin A,$$

The intensity is, $$I = |E_A|^2 = I_0(1 + \alpha \cos 2A + \beta \sin 2A).$$

$\alpha$ and $\beta$ are the Fourier coefficients of light intensity I, its value can be obtained by numerical calculation. They can be expressed as:

$$\alpha = \frac{|\rho_{pp} + \rho_{ps}\tan P|^2 - |\rho_{sp} + \tan P|^2}{|\rho_{pp} + \rho_{ps}\tan P|^2 + |\rho_{sp} + \tan P|^2};$$

$$\beta = \frac{2\text{Re}[(\rho_{pp} + \rho_{ps}\tan P)(\rho_{sp} + \tan P)]}{|\rho_{pp} + \rho_{ps}\tan P|^2 + |\rho_{sp} + \tan P|^2}.$$

When $r_{ps} = r_{sp} = 0$, i.e., $\rho_{ps} = \rho_{sp} = 0$, the formulas for calculating the sample with isotropic film can be expressed as:

$$\alpha = \frac{|\rho_{pp}|^2 - |\tan P|^2}{|\rho_{pp}|^2 + |\tan P|^2} = \frac{\tan^2\psi - \tan^2 P}{\tan^2\psi + \tan^2 P};$$

$$\beta = \frac{2\text{Re}(\rho_{pp}\tan P)}{|\rho_{pp}|^2 + |\tan P|^2} = \frac{2\tan\psi\cos\Delta\tan P}{\tan^2\psi + \tan^2 P}.$$

Wherein, $\tan\psi$ is the amplitude ratio of $r_{pp}$ and $r_{ss}$, $\Delta$ is the phase difference of $r_{pp}$ and $r_{ss}$.

In ellipsometry measurement method, the spectra of Fourier coefficients $\alpha$ and $\beta$ can be calculated by ellipsometry, they are directly correlated to the elements $\rho_{pp}$, $\rho_{ps}$ and $\rho_{sp}$ of the normalized Jones matrix. Through mathematical modelling and curve regression fitting, one can get the film thickness and optical constants of materials, and/or the critical dimension (CD) properties or three-dimensional profile of the periodical structure of the sample.

Figure 7:
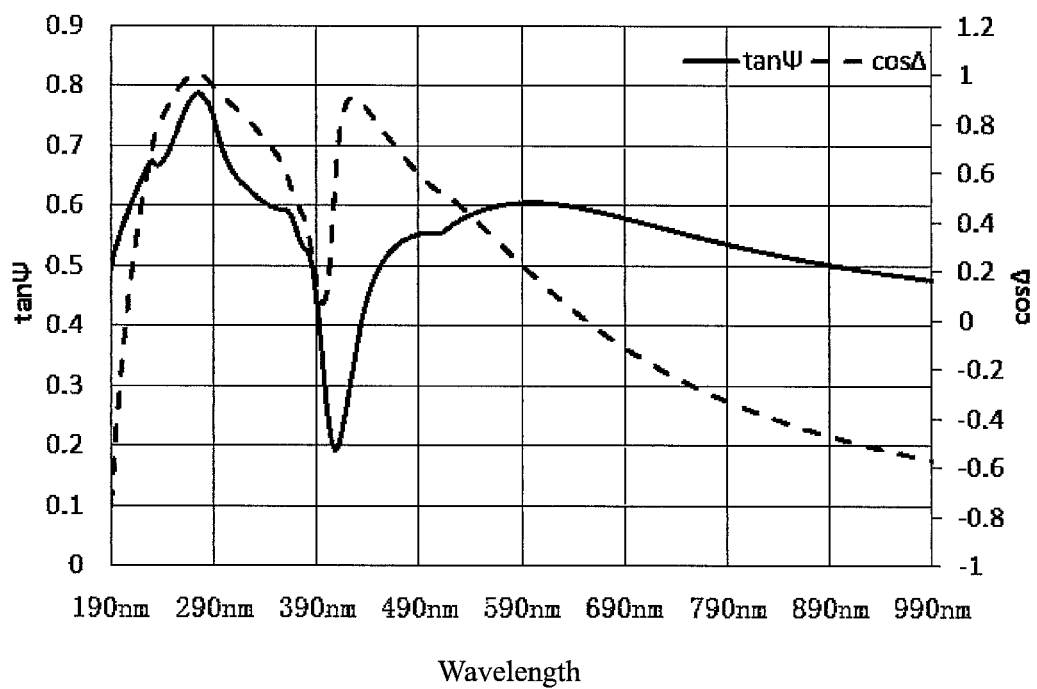
FIG. 7 is a schematic drawing to show the spectra of the reflectivity amplitude ratio of the TE and TM modes and the phase difference between the TE and TM modes in ellipsometry measurements.

The process of system calibration can be referred to HANDBOOK OF ELLIPSOMETRY, Harland G. Tompkins, 2005; Spectroscopic Ellipsometry Principles and Applications, Hiroyuki Fujiwara, 2007. Taking the structure shown in FIG. 5 as an example, when $\phi=0$, $\theta=60°$, ie., in this angle, $r_{ps} = r_{sp} = 0$, the spectra of amplitude ratio and phase difference are shown in FIG. 7.

Next, with the assistance of the figures, the embodiments based on the oblique incidence broadband spectroscopic polarimeter in present invention are described in detail.

First Embodiment

Figure 8:
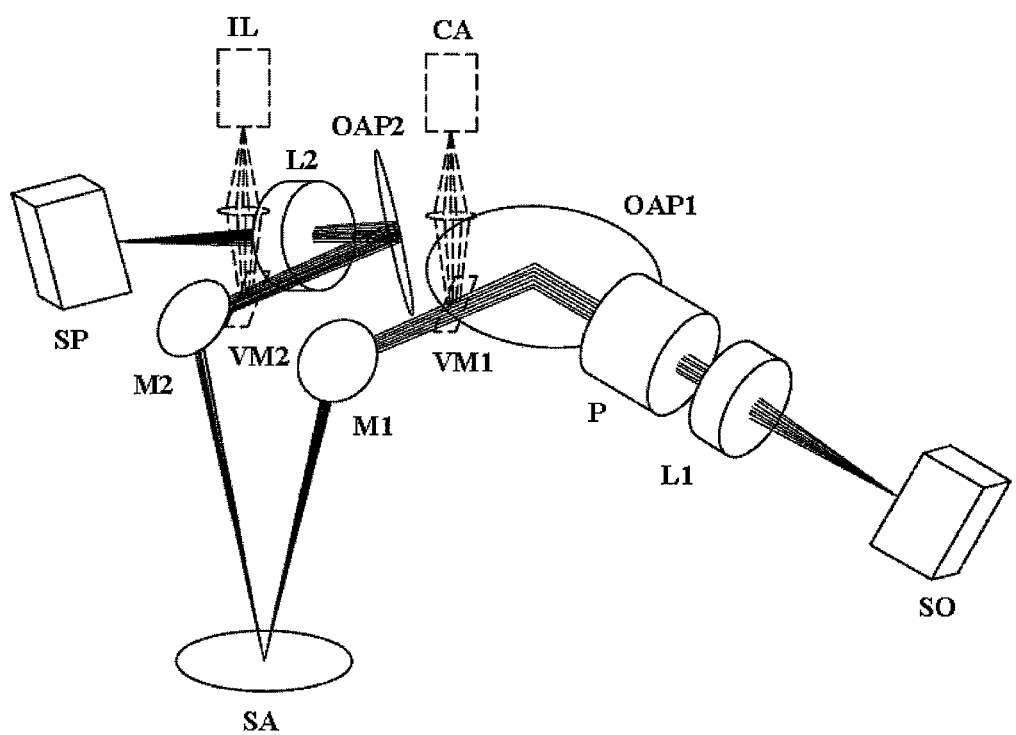
FIG. 8 is a schematic drawing to show the first embodiment of the oblique incidence broadband spectroscopic polarimeter of the present invention.

FIG. 8 shows the first embodiment of the oblique incidence broadband spectroscopic polarimeter of the present invention. As shown in FIG. 8, the oblique incidence broadband spectroscopic polarimeter includes a broadband spot light source SO, lens L1 and L2, off-axis parabolic mirrors OAP1 and OAP2, a polarizer P, a broadband spectrometer SP, flat reflector mirrors M1 and M2, a sample SA and an optional vision system. The vision system which can display patterns of the surface of the sample SA and the detecting beam spot on the sample surface simultaneously, is composed of movable flat reflector mirrors VM1 and VM2, the illumination light unit IL and the imaging unit CA.

The broadband spot light source SO placed at the focus of the focusing lens L1, beam emitted from the broadband spot light source SO is converged into a collimated beam after passing through the focusing lens L1. After passing through the polarizer P, the collimated beam enters the off-axis parabolic mirror OAP1 at an incident angle of 45 degree, which deflects it for in 90 degree in the incident plane. The beam reflected by the off-axis parabolic mirror OAP1 is a focused beam with chief ray in horizontal plane. The focused beam enters the flat reflector mirror M1 at 45 degree, which deflects it in 90 degree in the incident plane, then enters downward to the sample and is focused on the sample surface. The light reflected from the sample surface, to the flat reflector mirror M2, the off-axis parabolic mirror OAP2 and the lens L2, forms a focused beam, then enters the broadband spectrometer SP. Wherein, the plane consisted by the off-axis parabolic mirrors OAP1 and OAP2 and flat reflector mirrors M1 and M2, is parallel to the sample plane, and perpendicular to the incident plane formed by the incident points on flat reflector mirrors M1, M2 and sample SA, as well as to the plane consisted by broadband spot light source SO, broadband spectrometer SP, off-axis parabolic mirrors OAP1, OAP2, focusing lens L1, L2 and polarizer P. In the plane consisted by off-axis parabolic mirrors OAP2, OAP2, and flat reflector mirrors M1, M2, the chief ray of detecting beam and chief ray of reflected beam of sample SA are parallel to each other.

In addition, the tilt angle and/or spatial position of the flat reflector mirrors M1 and M2 are adjustable; the broadband spectroscopic polarimeter may also include an adjustable sample platform for loading the sample, based on the above focus principle. The flat reflector mirrors M1 and M2 can be adjusted to achieve focus. For example, the flat reflector mirrors M1 and M2 can move along propagation direction or its opposite direction of the chief ray of detecting beam and reflector beam of sample SA in the plane consisted by off-axis parabolic mirrors OAP1 and OAP2 and flat reflector mirrors M1 and M2. And the flat reflector mirrors M1 and M2 can also pivots on a shaft through the direction. In the process of adjustment, the flat reflector mirrors M1 and M2 can be mirror symmetry relative to the plane which passes through the normal line in the focus position on sample SA, and perpendicular to the incident plane on the sample SA. When adjusting focus in the direction of normal line of the surface, flat reflector mirrors M1 and M2 are moved along the same direction, the tilt of flat reflector mirrors M1 and M2 are symmetrically adjusted relative to the sample surface, i.e., the flat reflector mirrors M1 and M2 rotate about the axis, which is a shaft through the direction of chief ray which is parallel to the sample surface. At the same time, the sample SA also moves along the same direction on the sample surface.

In this embodiment, the flat reflector mirror M1 and off-axis parabolic mirror OAP1 meet the condition that their incident planes are perpendicular to each other. When the linear polarized direction of the detecting beam pass through polarizer P is parallel or perpendicular to the above incident plane, the detecting beam is a single p-polarization or s-polarization relative to the flat reflector mirror M1 and the off-axis parabolic mirror OAP1, so when the detecting beam propagates in the optical path between the polarizer P and the surface of the sample SA, its linear polarized properties remain unchanged. In this embodiment, the incident plane of detecting beam on flat reflector mirror M1 is perpendicular to the incident plane on off-axis parabolic mirror OAP1; on this condition, when the azimuth angle of detecting beam leads to that the sample has $r_{ps}=r_{sp}=0$, the beam reflected by the sample surface will remains the original single p-polarization or s-polarization. When propagates in the optical path between the sample SA and spectrometers P, the p- or s-polarized light reflected by the sample experience the same changes as the p- or s-polarized light reflected by the reference sample. After passing through the flat reflector mirror M2 and off-axis parabolic mirror OAP2, the reflected beam enters the spectrometers SP.

For the sample with Jones matrix element $r_{ps}=r_{sp}=0$, if the oblique incidence spectroscopic polarimeter has only one polarizer, the sample can be measured by absolute reflectivity measurement. i.e., by adjusting the polarizer, the absolute reflectivity of the sample and be obtained when the detecting beam only contains p-polarization or only contains s-polarization relative to incident plane of the sample. When the detecting beam contains only p- or s-polarized light and the relations between the incident azimuth of detecting beam and sample meet $r_{ps}=r_{sp}=0$, the beam reflected by the sample surface will also only contains p or s polarization, the coupled efficiency from the sample to the spectrometer SP is independent to the sample. The reflected beam with a single polarized state (s-light or p-light) from the reference sample and sample to spectrometers SP experience the same polarization changes, so it is not required to maintain the polarization properties and there is no restriction on the polarization-sensitive of optical components. In accordance with the absolute reflectivity measurement methods described above, the oblique incidence spectroscopic polarimeter can measure the Jones matrix elements $r_{ss}$, $r_{pp}$, corresponding to absolute reflectivity of the TE and TM in the three-dimensional periodic structures. The invention can also include a computing unit which is to do curve regression fit of the mathematical model of reflectivity and calculate the optical constants and film thickness and/or the critical dimensions (CD) or three-dimensional profile of the periodic structure of the sample.

In this embodiment, the flat reflector mirror also plays a role of light zipping to making optical system more compact, making the large inclination angle optical system has smaller size than the optical system adopting lens or single mirror, for example: U.S. Pat. No. 5,608,526 and U.S. Pat. No. 7,663,768. Compared with the normal incidence broadband spectroscopic polarimeter described in Chinese patent application No. 201,110,032,744.8, the size of optical system of oblique incidence broadband spectroscopic polarimeter in this embodiment is approximately doubled.

Broadband spot light source SO emits broadband divergence beam, the spectrum of broadband beam is usually in the deep ultraviolet to near infrared range (from about 190 nm to 1100 nm wavelength range). In practice, broadband spot light source SO can be a xenon lamp, a deuterium lamp, a tungsten lamp, a halogen lamp, a mercury lamp, a composite broadband light source including deuterium lamp and tungsten lamp, a composite broadband light source including tungsten lamp and halogen lamp, a composite broadband light source including mercury lamp and xenon lamp or a composite broadband light source containing deuterium lamp, tungsten lamp and halogen lamp (U.S. Pat. No. 6,667,805). The beam emits from the broadband light source can be natural light (i.e., the degree of polarization equal to zero). However, the broadband point source can also be natural spot light source with zero degree polarization obtained from a depolarizer. Examples for broadband spot light source SO include Ocean Optics products HPX-2000, HL-2000 and DH2000, and Hamamatsu company product L11034, L8706, L9841 and L10290. Broadband spectrometer can be charge-coupled device (CCD) or photodiode array (PDA), for example, the Ocean Optics QE65000 spectrometer, or the B & W Teck, Cypher spectrometer.

The sample is usually loaded in a movable platform with X-Y-Z-Theta or R-Theta-Z coordinate. In semiconductor industry, the sample size can be a diameter of 8 inches (200 mm) or 12 inches (300 mm) wafers. In the flat panel display industry, the sample usually has a size of more than one meter. Due to the reasons such as film stress on wafer, the wafer may be uneven. For a large-scale sample, the sample surface may be distorted, or the sample platform may be uneven. Therefore, during sample testing, to improve the accuracy of measurement and keep relatively fast speed, each measurement point needs to be automatically refocused.

Before the measurement, take half of the removable flat reflector mirror VM1 into the light path, and the whole removable flat reflector mirror VM2 into the light path. After reflected by flat reflector mirror, the reflected beam of detecting beam and illumination beam of the pattern recognition system on the sample surface both obtained by pattern recognition system. Then by moving the sample platform, one can direct the light spot to the measured pattern. By calculating the image clarity on the sample surface, one can adjust focus on the sample by taking the calibrated image recognition system as a benchmark. Therefore, in addition to judging the focus of detecting beam on sample by observing the changes of light intensity in the spectrometer, this embodiment also have another method, that is, judge the focus by observing the image clarity in the image recognition system. The coexistence of two focusing system improved the focus accuracy of the device and one can align the spot of detecting beam with the pattern in sample surface. Moreover, in the focusing process, the movable flat reflector mirrors VM1 and VM2 do not need to move with the flat reflector mirrors M1 and M2. When the movable flat reflector mirrors VM1 and VM2 move away from the optical path, it doesn't have any influence to the optical path, one can measure the spectrum. In addition, the splitting element can achieve the volume angle (the angle of the detecting beam relative to the sample surface) symmetric uniform distribution which can improve the accuracy of measurement or simplify the calculation model.

In addition, in this embodiment, the position of broadband spot light source SO and the broadband spectrometer SP location are interchangeable, but applies only to the sample with Jones matrix element $r_{ps}=r_{sp}=0$. In this case, the polarizer P is equivalent to the polarizer; one can measure the reflected light intensity of the sample and reference sample in the two orthogonal polarized directions corresponding to the directions of p and s polarization of reflected beam on the sample surface, and then calculate the absolute reflectivity of the sample on the two polarization directions.

In addition, in this embodiment, taking the sample SA as splitting point, except polarizer P, the off-axis parabolic mirror the OAP2 and lens L2 in the optical path can be replaced by other forms of focusing unit (for example, the focusing unit consist of several lens, or the toroidal mirror, etc.).

In addition, in this embodiment, one can place mirrors between the broadband spot light source SO and the focusing lens L1, and between the broadband spectrometers SP and the focusing lens L2, so that the structure is more compact and easier to be implemented by folding the optical path.

Not only can the broadband spectroscopic polarimeter in this embodiment focus through simple operation, but also it can maintain the linear polarized properties of the detecting beam.

Based on this embodiment and the above principle to maintain the polarization properties, other equivalents of this embodiment may be derived.

Second Embodiment

Figure 9:
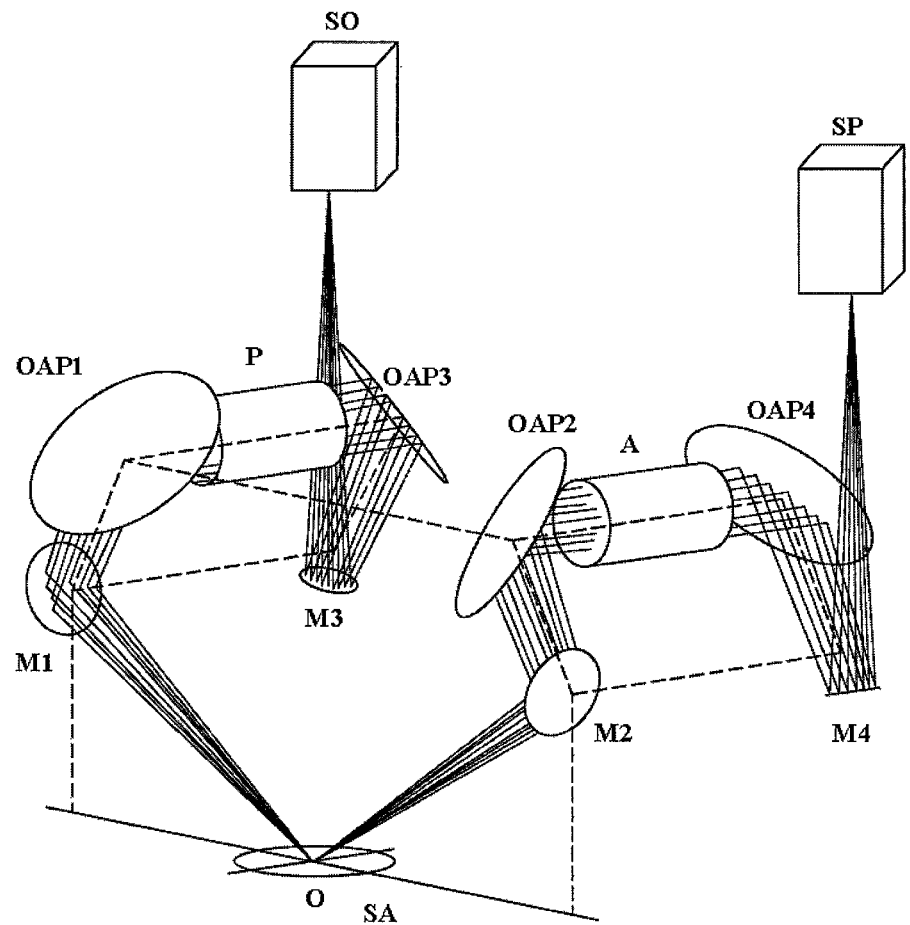
FIG. 9 is a schematic drawing to show the second embodiment of the oblique incidence broadband spectroscopic polarimeter of the present invention.

FIG. 9 shows the second embodiment of the oblique incidence broadband spectroscopic polarimeter of the present invention. As shown in FIG. 9, it includes a broadband spot light source SO, a broadband spectrometer SP, the off-axis parabolic mirrors OAP1, OAP2, OAP3, and OAP4, a polarizer P, a analyzer A, the flat reflector mirrors M1, M2, M3 and M4, and a sample SA.

The broadband spot light source SO placed at the image of the focus of the off-axis parabolic mirror OAP3 in flat reflector mirror, after reflected by the flat reflector mirror M3, the beam emitted from the broadband spot source SO enters the off-axis parabolic mirror OAP3 at 45-degree incident angle, the off-axis parabolic mirror OAP3 deflect the divergent beam 90 degree in the incident plane, and make it change into a collimated beam which propagates along the horizontal plane. After the polarizer P, the collimated beam enters the off-axis parabolic mirror OAP1 at 45 degree incident angle, the off-axis parabolic mirror OAP1 make the collimated beam deflecting 90 degree in the incident plane, and forming a focused beam at an angle 60 degree to horizontal plane and propagate within the sample vertical plane, after reflected by the flat reflector mirror M1, the focused beam deflect 90 degree, and then is oblique incident on the sample surface at 60 degree and focus on the sample surface. The beam reflected from the sample surface, to the symmetrical flat reflector mirror M2, an off-axis parabolic mirror OAP2, an analyzer A, an off-axis parabolic mirror OAP4, and a flat reflector mirror M4, form a focused beam. After reflected by the splitting element BP, 50 percent of the focused beam enters the broadband spectrometer SP. Wherein, the plane consisting of the off-axis parabolic mirrors OAP1 OAP2, OAP3 and OAP4 is parallel to the plane of sample SA, and perpendicular to the incident plane on the sample SA, which is formed mirrors M1, M2, off-axis parabolic mirror OAP1 and OAP2 and the incident point O on the sample SA, and perpendicular to the plane consisting of the broadband spot light source SO, the broadband spectrometers SP, the off-axis parabolic mirrors OAP3 and OAP4, the flat reflector mirrors M3 and M4. In the plane constituted by the off-axis parabolic mirror OAP1, OAP2, OAP3 and OAP4, the beams are parallel to each other.

In addition, the tilt angle and/or spatial position of the flat reflector mirrors M1 and M2 are adjustable, the broadband spectroscopic polarimeter may also include an adjustable sample platform for loading the sample. Based on the above focus principle, the flat reflector mirrors M1 and M2 can be adjusted to realize focus. For example, as the method of moving distance and inclination angle of flat reflector mirrors described above, the flat reflector mirrors M1 and M2 can be moved the same distance symmetrically along the directions of the chief rays of beam between M1 and OAP1, and between M2 and OAP2; and rotating the same angles symmetrically in the sample incident plane formed by the flat reflector mirrors M1, M2, the off-axis parabolic mirrors OAP1, OAP2, and the incident point O on the sample SA.

In this embodiment, the flat reflector mirror M1 and off-axis parabolic mirror OAP1 meet the condition that the incident angles of the beam are the same and the incident planes are perpendicular to each other, the flat reflector mirror M2 and off-axis parabolic mirror OAP2 meet the condition that the incident angles of the beam are the same and the incident planes are perpendicular to each other, and the incident planes of flat reflector mirror M1, M2, and sample SA are the same plane. If the linear polarized direction of the detecting beam passed through polarizer P is parallel or perpendicular to the incident plane, then the detecting beam will be single p- or s-polarization relative to the flat reflector mirror M1 and off-axis parabolic mirror OAP1, so when the detecting beam propagates in the optical path between the polarizer P and the surface of sample SA, its linear polarization remains unchanged. In this embodiment, the incident plane of detecting beam on flat reflector mirror M1 coincides to the incident plane on sample surface, and coincides to the incident plane on flat reflector mirror M2 of the beam reflected by sample SA. Under this condition, define the p or s direction of sample is perpendicular or parallel to the polarized direction of detecting beam, the direction of p- or s-polarization of the sample reflected beam is parallel or perpendicular to the incident plane on the flat reflector mirror M2 of the sample reflected beam. Therefore, in the optical path between the surface of sample SA and the analyzer A, the p- or s-polarization of the beam reflected by the reference sample and the sample experience the same changes. If the polarized direction of the reflected beam passed through the analyzer A is parallel or perpendicular to the above incident plane, one can measure p- or s-polarization of the beam reflected by the sample surface respectively. Compared with the first embodiment, due to the addition of the analyzer A, this embodiment can measure the samples with $r_{ps}$, $r_{sp}$ not equal to zero; the p and s directions of sample are defined according to the incident azimuth of detecting beam. When implementing the absolute reflectivity measurement, one can measure all of the four Jones matrix elements, that is, the absolute reflectivity of sample when polarizer P and analyzer A is set correspond to the four cases that the polarization in incident plane are p&p, p&s, s&p and s&s.

In this embodiment, the flat reflector mirror M1 and off-axis parabolic mirror OAP1 meet the condition that the incident angles of the beam are the same and the incident planes are perpendicular to each other, the flat reflector mirror M2 and off-axis parabolic mirror OAP2 meet the condition that incident angles of the beam are the same and the incident planes are perpendicular to each other. If the flat reflector mirror M1 and off-axis parabolic mirror OAP1 have the same reflective material and coating structure, when focusing on the surface of sample SA at oblique incidence, the polarization properties of the detecting beam remains unchanged. If the flat reflector mirror M2 and off-axis parabolic mirror OAP2 have the same reflective material and coating structure, when entering the analyzer A, the polarization of the beam reflected by the sample remains unchanged. So, the linear polarized direction of detecting beam can be adjusted by rotating the polarizer P. After passing through the flat reflector mirror M2 and off-axis parabolic mirror OAP2, the beam reflected by the sample SA enters the analyzer A, the analytic angle is adjusted by the analyzer A. It can be seen that the focusing system and focusing process do not affect the polarization between polarizer P and the sample surface, as well as between the sample surface and analyzer A.

Since the polarization of the beam after polarizer P remains unchanged when focusing on the surface of the sample SA at oblique incidence, and the polarization of the beam reflected from sample surface remains unchanged before entering the polarizer A, the ellipsometry measurement method can also be implemented in this embodiment. When ellipsometry measurement is implemented, it's not required to switch between the reference sample and the measurement sample. As mentioned above, the detailed measurement method can be achieved by fixing the polarizer P and rotating the analyzer A, fixing the analyzer A and rotating the polarizer P, or rotating the analyzer A and fixing the polarizer P at a certain rotational frequency ratio. The oblique incidence broadband spectroscopic polarimeter can measure the $r_{pp}$, $r_{ps}$, $r_{sp}$ and $r_{ss}$ according to the absolute reflectivity measurement method described above, or calculate the spectra of the two Fourier coefficients α and β, the spectra are directly related to the elements $\rho_{pp}$, $\rho_{ps}$ and $\rho_{sp}$ of normalized Jones matrix. Through mathematical model calculation and curve regression fitting, one can get the optical constants and film thickness of sample materials, and/or the critical dimension (CD) or three-dimensional profile of the periodic structure of sample.

The same to first embodiment, this embodiment may also include an vision system.

In this embodiment, the focusing unit including flat reflector mirror M3 and off-axis parabolic mirror OAP3 can be replaced by a focusing lens. When the beam propagates between the broadband light source SO and the polarizer P, its polarization remains unchanged before entering polarizer P; the natural polarization of the broadband light source SO is maintained. The focusing unit including flat reflector mirror M4 and off-axis parabolic mirror OAP4 can also be replaced by a focusing lens. When propagating between analyzer A and the broadband spectrometer SP, the beam's polarization remains unchanged before entering polarizer P; the linear polarization of the reflected beam after passing through the analyzer A is maintained before it enters the broadband spectrometer SP. The beneficial effects can be realized by partly eliminating the polarization sensitivity in the reflection system described above, and only the broadband spectrometer SP has the polarization sensitivity. The numerical correction caused by the system polarization sensitivity is thus simplified in this implementation.

In this embodiment, the flat reflector mirror M3 and off-axis parabolic mirror OAP3 may meet the condition that the incident angles are the same and the incident planes are perpendicular to each other, and have the same reflective materials and coating structure. The flat reflector mirror M4 and off-axis parabolic mirror OAP4 may meet the condition that the incident angles are the same and the incident planes are perpendicular to each other, and have the same reflective materials and coating structure. The system polarization sensitivity caused by the reflection can be partly eliminated, and only the sensitivity of the broadband spectrometer SP to polarization state is presented. Therefore, the numerical correction is simplified in this implementation. Due to all of the optical propagation are reflective in the optical system, this implementation also achieves the beneficial effects of achromatic in the range of broadband spectrum.

Third Embodiment

Figure 10:
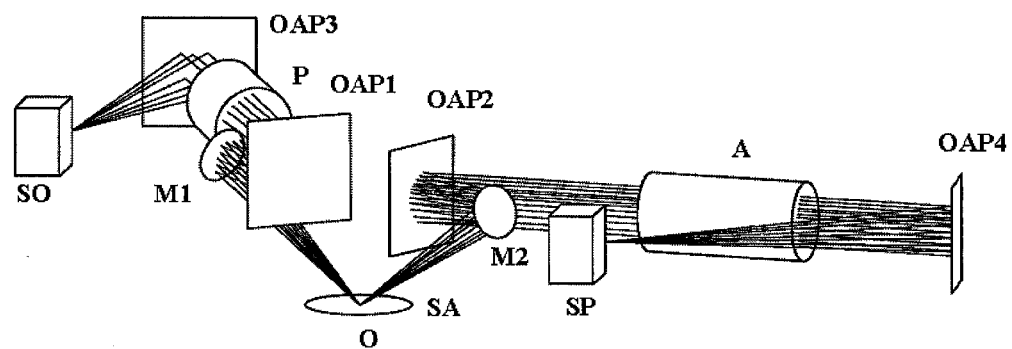
FIG. 10 is a schematic drawing to show the third embodiment of the oblique incidence broadband spectroscopic polarimeter of the present invention.

FIG. 10 shows the third embodiment of the oblique incidence broadband spectroscopic polarimeter of the present invention. As shown in FIG. 10, it includes a broadband spot light source SO, a broadband spectrometer SP, the off-axis parabolic mirrors OAP1, OAP2, OAP3, and OAP4, a polarizer P, a analyzer A, the flat reflector mirrors M1 and M2, and sample SA.

The broadband spot light source SO place at the focus of the off-axis parabolic mirror OAP3, the beam emitted from the broadband spot light source SO is incident to the off-axis parabolic mirror OAP3 at an angle of 15 degree, which deflects the divergent beam 30 degree in the incident plane, and makes it changing into a collimated beam propagates in the horizontal plane. After polarizer P, the collimated beam enters the off-axis parabolic mirror OAP1 at incident angle of 15 degree, then deflects 30 degree in the incident plane and changes into a focused beam, the chief ray of the focused beam propagates in the horizontal plane. After entering the flat reflector mirror M1 at an incident angle of 15 degree, the focused beam deflects 30 degree in the incident plane, then forms a focused beam downward-sloping propagates in the plane vertical to sample, and focus on the sample surface at an oblique incidence. The beam reflected by the sample surface, to the flat reflector mirror M2, the off-axis parabolic mirror OAP2, the analyzer A, the off-axis parabolic mirror OAP4 which are mirror symmetrical to the above structure, then enters the broadband spectrometer SP. Wherein, the plane consisting of the off-axis parabolic mirror OAP1, OAP2, OAP3, and OAP4, broadband spot light source SO, and broadband spectrometer SP is parallel to the sample plane, and perpendicular to the incident plane formed by the incidence points on flat reflector mirrors M1, M2, off-axis parabolic mirrors OAP2, OAP2, and on the sample SA.

In this embodiment, the focusing is realized through the method described in the second embodiment.

In this embodiment, the flat reflector mirror M1 and off-axis parabolic mirror OAP1 meet the condition that incident angles of the beam are the same and the incident planes are perpendicular to each other; the flat reflector mirror M2 and off-axis parabolic mirror OAP2 meet the condition that the incident angles of the beam are the same and the incident planes are perpendicular to each other. If the flat reflector mirror M1 and off-axis parabolic mirror OAP1 have the same reflective material and coating structure, when focusing on the surface of sample SA at oblique incidence, the polarization properties characteristics of the detecting beam remains unchanged relative to that of passing through the polarizer P. If the flat reflector mirror M2 and off-axis parabolic mirror OAP2 have the same reflective material and coating structure, the polarization of the beam reflected by the sample remains unchanged before entering the analyzer A. Therefore, the linear polarized direction of the detecting beam can be adjusted by rotating the polarizer P. The beam reflected by the sample SA pass through the flat reflector mirror M2 and off-axis parabolic mirror OAP2, and then enters the analyzer A, the analytic angle is adjusted by the analyzer A. It can be seen that the focusing system and focusing process do not affect the polarization between polarizer P and the sample surface, as well as between the sample surface and analyzer A.

Compared to the second embodiment, this embodiment employs the optical structure in which the beam enters the mirror at smaller incident angle (15 degree). It is shown that the polarization change caused by reflection at small incident angle is lower than that of the bigger incident angle. Therefore, under the condition that two mirrors have the approximately same reflective material and coating structure, and the incident angles of the chief rays are the same and the incident planes are perpendicular to each other, the polarization intensity and phase changes in this embodiment of using incident angle of 15 degree is much smaller than that of 45 degree; it has better effect for using incident angle of 15 degree than of 45 degree. As mentioned above, compared to the method that the polarization is maintained by using only a single mirror described in U.S. Pat. No. 5,608,526, the method described above is better in maintaining the polarization. Therefore, the technical proposal proposed in the present invention is superior to the prior art. It can reduce the error of polarization maintenance caused by the long focal curved-surface, spatial location, coating process, material compatibility, mirror flatness, etc, and improve the measurement accuracy.

This embodiment can implement the same measurements described in the second embodiment.

As in the first embodiment, this embodiment may also include an vision system.

Compared to the second embodiment, in this embodiment, one can add flat reflector mirror M3 (not shown) between the off-axis parabolic mirror OAP3 and the broadband light source SO, add flat reflector mirror M4 (not shown) between the off-axis parabolic mirror OAP4 and the broadband spectrometer SP. The flat reflector mirror M3 and off-axis parabolic mirror OAP3 may meet the condition that the incident angles are the same and the incident planes are perpendicular to each other, and have the same reflective materials and coating structure; the flat reflector mirror M4 and off-axis parabolic mirror OAP4 may meet the condition that the incident angles are the same and the incident planes are perpendicular to each other, and have the same reflective materials and coating structure. The system polarization sensitivity caused by the reflection can be partly eliminated, and only the polarization sensitivity of broadband spectrometer SP is presented. Therefore, the numerical correction caused by the system polarization sensitivity is simplified. This implementation also achieves the beneficial effects of achromatic in the range of broadband spectrum.

Although the tilt angle and/or spatial position of flat reflector mirrors M1 and M2 in the above embodiments are adjustable, they also can be fixed. The oblique incidence broadband spectroscopic polarimeter in present invention may also include a computing unit, which is used to calculate the optical constants of sample material, and/or the critical dimensions properties or three-dimensional profile of the periodic micro-structure. Moreover, the oblique incidence broadband spectroscopic polarimeter in present invention may also include a rotation control device which is used for controlling polarization direction of the polarizer.

The oblique incidence broadband spectroscopic polarimeter in present invention is not limited to the specific forms disclosed in the above embodiments; the broadband spectroscopic polarimeter can be all kinds of deformation as long as in accordance with the general concepts describe above. The broadband spectroscopic polarimeter in the present invention can be applied to the measurement of semiconductor thin films, optical masks, metal films, dielectric films, glass (or coating), laser mirrors, thickness and optical constants of organic thin film, and critical dimension and three-dimensional profile of periodic structures consisting of these materials, in particular, can be applied to measure all dimensions of three-dimensional structures with one and two dimensional periodicity and formed by multilayer films in a plane and optical constants of layers of material.

This invention is not limited to the disclosed exemplary embodiments. The scope of the claims shall have wider range of interpretation, including all such modifications and equivalent structures and functions based on the concepts described above.

What is claimed is:

1. An oblique incidence broadband spectroscopic polarimeter comprising a light source, a first focusing unit, a first polarizer, a first curved reflector element, a first flat reflector element, a second flat reflector element, a second focusing unit and a detector unit, wherein, the first focusing unit is used for focusing a beam from the light source into a collimated beam;
the first polarizer is used for changing the collimated beam into a polarized beam;
the first curved reflector element is used for focusing the polarized beam and reflect the polarized beam to the first flat reflector element;
the first flat reflector element is used for focusing the polarized beam from the first curved reflector element making the focused beam oblique incident on the sample;
the second flat reflector element is used for reflecting the beam reflected from the sample to the second focusing unit;
the second focusing unit is used for focusing the reflected beam from the second flat reflector element and making the reflected beam incident on the detector unit; and
the first flat reflector element and the first curved reflector element meet the condition that incidence planes of the beams are perpendicular or parallel to each other.

2. The oblique incidence broadband spectroscopic polarimeter of claim 1, further comprising a second curve reflector element and a second polarizer, the second curved reflector element set in the optical path between the second flat reflector element and the second polarizer, the second polarizer is set in the optical path between the second curved reflector element and the second focusing unit, wherein, the second curved reflector element is used for receiving a reflected beam from the second flat reflector element and focus the reflected beam into collimated beam;
the second polarizer is used for changing the collimated beam from the second curved reflector element into a polarized beam;
the second focusing element is used for making the polarized beam from the second polarizer focus and incident on the detector unit; and
the second flat reflector element and the second curved reflector element meet the condition that incidence planes of the beams are perpendicular or parallel to each other.

3. The oblique incidence broadband spectroscopic polarimeter of claim 2, wherein the first flat reflector element and the first curved reflector element have the same reflective materials and coatings structure and meet the condition that incidence angles of the beams are same and the incident planes are perpendicular to each other; and the second flat reflector element and the second curved reflector element have the same reflective materials and coatings structure and meet the condition that incidence angles of the beams are same and the incident planes are perpendicular to each other.

4. The oblique incidence broadband spectroscopic polarimeter of claim 3, wherein the first focusing unit includes a third curved reflector element, the second focusing unit includes a fourth curved reflector element, wherein, the light source is set in the focus point of the third curved reflector element, making that a beam from the light source changed into a collimated beam after the reflection of the third curved reflector element; and
the fourth curved reflector element is used for receiving the polarized beam from the second polarizer and focusing the polarized beam to the detector unit.

5. The oblique incidence broadband spectroscopic polarimeter of claim 4, wherein the first curved reflector element, the second curved reflector element, the third curved reflector element and the fourth curved reflector element are off-axis parabolic mirror reflector element or toroidal mirror reflector element.

6. The oblique incidence broadband spectroscopic polarimeter of claim 3, wherein the first focusing unit includes a third flat reflector element and a third curved reflector element, the second focusing unit includes a fourth curved reflector element and a fourth flat reflector element, wherein, the light source is set at the image of the focus point of the third curved reflector element in the third flat reflector element, making that the beam from the light source change into a collimated beam after reflected by the third flat reflector element and the third curved reflector element;

the fourth curved reflector element is used for receiving the polarized beam from the second polarizer and focus the second polarizer to the fourth flat reflector element;

the fourth flat reflector element is used for reflecting the polarized beam from the fourth curved reflector element to the detector unit;

the third flat reflector element and the third curved reflector element have same reflective materials and coatings structure and meet the condition that incidence angles of beams are same and the incident planes are perpendicular to each other; and the fourth flat reflector element and the fourth curved reflector element have the same reflective materials and coatings structure and meet the condition that incidence angles of beams are same and the incident planes are perpendicular to each other.

7. The oblique incidence broadband spectroscopic polarimeter of claim 2, wherein incident angle on the first flat reflector element and the first curved reflector element, and on the second flat reflector element and the second curved reflector element are same, moreover, the range of angle is from 10 degree to 45 degree.

8. The oblique incidence broadband spectroscopic polarimeter of claim 2, further comprising at least one aperture which is placed between the first polarizer and the second polarizer, and used for avoiding the e light generated from the first polarizer incident to the sample surface and its reflected beam incident on the second polarizer.

9. The oblique incidence broadband spectroscopic polarimeter of claim 2, wherein the first curved reflector element and the second curved reflector element are off-axis parabolic mirror reflector element or toroidal mirror reflector element.

10. The oblique incidence broadband spectroscopic polarimeter of claim 2, wherein the first polarizer and the second polarizer can be thin-film polarizer, Glan-Thompson prism polarizer, Rochon prism polarizer, Glan-Taylor prism polarizer or Glan laser polarizer.

11. The oblique incidence broadband spectroscopic polarimeter of claim 10, further comprising the polarizer rotation control devices which are used for controlling polarization direction of the first polarizer and the second polarizer.

12. The oblique incidence broadband spectroscopic polarimeter of claim 1, wherein the structure of optical path between the light source and sample surface and the structure of optical path between the sample surface and the detector unit are mirror symmetric relative to the following plane: the plane going through the normal line at the focus position on the sample, and vertical to the incident plane on the sample.

13. The oblique incidence broadband spectroscopic polarimeter of claim 1, wherein the first curved reflector element is off-axis parabolic mirror reflector element or toroidal mirror reflector element.

14. The oblique incidence broadband spectroscopic polarimeter of claim 1, wherein the tilt angle and/or spatial position of the first flat reflector element and second flat reflector element are adjustable.

15. The oblique incidence broadband spectroscopic polarimeter of claim 14, wherein the first flat reflector element and the second flat reflector element can move along the propagation direction of chief ray of the focused beam which focus on the sample surface, and/or the first flat reflector element and the second flat reflector element can tilt relative the chief ray direction of the focused beam, and/or the first flat reflector element and the second flat reflector element can rotate about the axis, which is the chief ray direction of the focused beam.

16. The oblique incidence broadband spectroscopic polarimeter of claim 14, wherein the first flat reflector element and the second flat reflector element are mirror symmetric or antisymmetric relative to the following plane: the plane go through the normal line on the focus of sample, and vertical to the incident plane on the sample.

17. The oblique incidence broadband spectroscopic polarimeter of claim 16, wherein the first flat reflector element and the second flat reflector element can move along a direction on the sample surface, and their tilt angle relative to the sample surface can be adjusted symmetrically, i.e., rotate about the chief ray direction of the focused beam that is focusing on the sample, which part is parallel to the sample surface, to ensure that the focus position on the sample surface is constant in another direction orthogonal to the direction, and at the same time, the sample may move along the direction on the sample surface.

18. The oblique incidence broadband spectroscopic polarimeter of claim 1, further comprising an adjustable sample platform which is used for loading the sample.

19. The oblique incidence broadband spectroscopic polarimeter of claim 1, further comprising an vision system, wherein, the vision system is set in the optical path between the first curved reflector element and first flat reflector element, and in the optical path between the second flat reflector element and second focusing unit;

the vision system includes at least two adjustable flat reflector elements, an illumination unit and an imaging unit; and the focusing can be adjusted through observing the light intensity of the detector unit and/or the image clarity of the pattern in the image system.

20. The oblique incidence broadband spectroscopic polarimeter of claim 1, wherein the first polarizer is thin-film polarizer, Glan-Thompson prism polarizer, Rochon prism polarizer, Glan-Taylor prism polarizer or Glan laser polarizer.

21. The oblique incidence broadband spectroscopic polarimeter of claim 20, further comprising a polarizer rotation control device which is used for controlling polarization direction of the first polarizer.

22. The oblique incidence broadband spectroscopic polarimeter of claim 1, wherein the first focusing unit and the second focusing unit comprising at least one curved reflector element or at least one focusing lens.

23. The oblique incidence broadband spectroscopic polarimeter of claim 1, wherein the light source is a light source includes multiple wavelengths of light source.

24. The oblique incidence broadband spectroscopic polarimeter of claim 1, wherein the light source is xenon lamp, a deuterium lamp, a tungsten lamp, a halogen lamp, a mercury lamp, a composite broadband light source including deuterium lamp and tungsten lamp, a composite broadband light source including tungsten lamp and halogen lamp, a composite broadband light source including mercury lamp and xenon lamp or a composite broadband light source containing deuterium, tungsten and halogen, or, the light source is spot light source of natural light with zero degree polarization get from depolarizer.

25. The oblique incidence broadband spectroscopic polarimeter of claim 1, wherein the detector unit is spectrometer.

26. The oblique incidence broadband spectroscopic polarimeter of claim 1, further comprising calculation unit, the calculation unit is used for calculating the optical constants of sample material, film thickness, and/or the critical dimension properties or three-dimensional profile for analyzing the periodic structure of the sample.

27. The oblique incidence broadband spectroscopic polarimeter of claim 1, wherein the range of incident angle on the sample surface is from 5 degree to 75 degree.

28. An optical measurement system comprising anyone of oblique incidence broadband spectroscopic polarimeter of claim 1.

* * * * *